United States Patent
McKittrick et al.

(10) Patent No.: US 6,472,394 B1
(45) Date of Patent: Oct. 29, 2002

(54) MCH ANTAGONISTS AND THEIR USE IN THE TREATMENT OF OBESITY

(75) Inventors: Brian A. McKittrick, New Vernon, NJ (US); Jing Su, Scotch Plains, NJ (US); John W. Clader, Cranford, NJ (US); Shengjian Li, Belle Mead, NJ (US); Guihau Guo, Plainsboro, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/023,371

(22) Filed: Dec. 17, 2001

Related U.S. Application Data
(60) Provisional application No. 60/257,873, filed on Dec. 22, 2000.

(51) Int. Cl.[7] .................. C07D 401/06; C07D 405/06; A61K 31/4525; A61K 31/453
(52) U.S. Cl. .................. 514/249; 514/266.22; 514/314; 514/321; 514/322; 514/330; 514/331; 544/283; 544/353; 546/168; 546/175; 546/197; 546/198; 546/199; 546/225; 546/233; 546/234
(58) Field of Search .................. 544/283, 353; 546/168, 175, 197, 198, 199, 225, 233, 234; 514/249, 259, 314, 321, 322, 330, 331, 266.22

(56) References Cited

U.S. PATENT DOCUMENTS

| | | | |
|---|---|---|---|
| 5,908,830 A | 6/1999 | Smith et al. | 514/12 |
| 6,037,352 A | 3/2000 | Lowe et al. | 514/316 |

FOREIGN PATENT DOCUMENTS

| | | | |
|---|---|---|---|
| EP | 643 057 | | 3/1995 |
| WO | 99/00367 | | 1/1999 |
| WO | WO 00/47559 | * | 8/2000 |
| WO | 01/09137 | | 2/2001 |

OTHER PUBLICATIONS

Shimada et al, *Nature*, 396(1998), p. 670–673.
Mathre et al, *J. Org. Chem.*, 58(1993), p. 2880–2888.
Uekama et al, *J. Med. Chem.*, 40(1997), p. 2755–2761.
*Chem. Abstr.*, 39(1945), 4077–4078.
Armarego, *J. Chem. Soc.*, Part 1 (1962), p. 561–572.
Jonas et al, *Eur. J. Med. Chem.*, 28(1993), p. 141–148.

* cited by examiner

*Primary Examiner*—Deepak R. Rao
(74) *Attorney, Agent, or Firm*—Anita W. Magatti

(57) ABSTRACT

Disclosed are compounds represented by structural formula I:

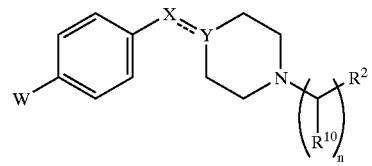

or a pharmaceutically acceptable salt, ester or solvate thereof, wherein

W is $R^1$—$CR^3R^{12}NR^4C(O)$— or $R^{11}C(O)NR^4$—;
the dotted line is an optional double bond;
X is —$CHR^8$—, —$C(O)$—, or —$C(=NOR^9)$—;
Y is

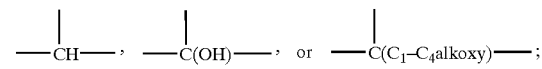

$R^1$ is optionally substituted cycloalkyl, cycloalkylalkyl, aryl, arylalkyl, heteroaryl, heteroarylalkyl, heterocycloalkyl or heterocycloalkyl-alkyl;
$R^2$ is optionally substituted aryl or heteroaryl;
$R^3$ is alkyl, aryl or heteroaryl;
$R^4$ and $R^{12}$ are H or alkyl;
$R^8$ is H, alkyl or alkoxyalkyl;
$R^9$ is H, alkyl or arylalkyl;
$R^{10}$ is H, alkyl or aryl;
$R^{11}$ is

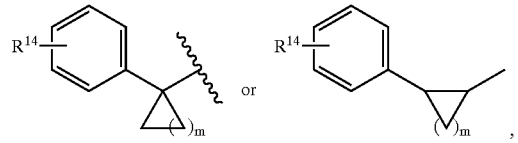

or, when $R^2$ is $R^6$-heteroaryl or $R^{10}$ is not H, $R^{11}$ can also be $R^5$-phenylalkyl;
n is 1–3 and m is 1–5; and
$R^{14}$ is 1–3 substituents selected from H, alkyl, halogen, —OH, alkoxy and $CF_3$;
and pharmaceutical compositions containing the compounds and methods of using the compounds in the treatment of eating disorders and diabetes.

12 Claims, No Drawings

MCH ANTAGONISTS AND THEIR USE IN THE TREATMENT OF OBESITY

CROSS REFERENCE TO RELATED APPLICATION

This application claims the benefit of US Provisional Application No. 60/257,873, filed Dec. 22, 2000.

BACKGROUND OF THE INVENTION

This invention relates to amide derivatives of 1,4-disubstituted piperidine antagonists for melanin-concentrating hormone (MCH) and their use in the treatment of obesity and diabetes.

MCH, a cyclic peptide, was first identified over a decade ago in teleost fish where it appears to regulate color change. More recently, MCH has been the subject of investigation for its possible role as a regulator of eating behavior in mammals. As reported by Shimada et al., Nature, Vol. 396 (Dec. 17, 1998), pp. 670–673, MCH-deficient mice have reduced body weight and leanness due to hypophagia (reduced feeding). In view of their findings, the authors have suggested that antagonists of MCH action may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist.

Piperidine-derivative muscarinic antagonists useful in the treatment of cognitive disorders such as Alzheimer's disease are disclosed in U.S. Pat. No. 6,037,352. In particular, U.S. Pat. No. 6,037,352 discloses compounds of the generic formula

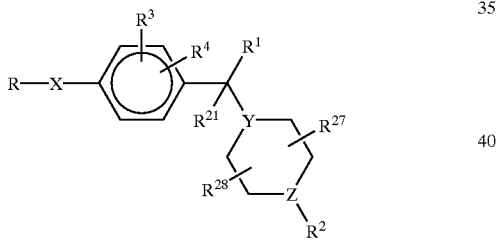

wherein, inter alia, Y is CH; Z is N; X is —NHCO—; R is substituted benzyl or cycloalkylalkyl; $R^1$, $R^{21}$, $R^3$, $R^4$, $R^{27}$ and $R^{28}$ are each hydrogen; and $R^2$ is optionally substituted cycloalkyl or arylalkyl. U.S. Pat. No. 6,037,352 does not disclose the use of the compounds for treating obesity or diabetes.

SUMMARY OF THE INVENTION

The present invention relates to compounds represented by structural formula I:

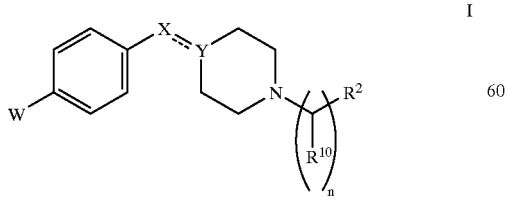

or a pharmaceutically acceptable salt, ester or solvate thereof, wherein

W is $R^1$—$CR^3R^{12}NR^4C(O)$— or $R^{11}C(O)NR^4$—;
the dotted line is an optional double bond;
X is —$CHR^8$—, —C(O)—, —C(=$NOR^9$)—, or, when the double bond is present, —$CR^8$=;
Y is

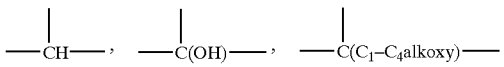

or, when the double bond is present,

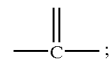

$R^1$ is $R^5$—$(C_3$–$C_8)$cycloalkyl, $R^5$—$(C_3$–$C_8)$cycloalkyl $(C_1$–$C_6)$alkyl, $R^5$-aryl, $R^5$-aryl-$(C_1$–$C_6)$alkyl, $R^5$-heteroaryl, $R^5$-heteroaryl$(C_1$–$C_6)$alkyl, $R^5$-heterocycloalkyl or $R^5$-heterocycloalkyl$(C_1$–$C_6)$alkyl;
$R^2$ is $R^6$-aryl or $R^6$-heteroaryl;
n is 1, 2 or 3;
$R^3$ is $C_1$–$C_6$ alkyl, aryl or heteroaryl;
$R^4$ is H or $C_1$–$C_6$ alkyl;
$R^5$ is 1–4 substituents independently selected from the group consisting of H, $C_1$–$C_6$ alkyl, halogen, —OH, $C_1$–$C_6$ alkoxy, —$CF_3$, $(C_1$–$C_6)$-alkoxycarbonyl, —$SO_2NHR^4$, —$C(O)NHR^4$, —$NR^4C(O)NHR^4$, —$NR^4C(O)R^4$, —$NR^4SO_2R^4$, $R^{13}$-phenyl and naphthyl;
$R^6$ is 1–4 substituents independently selected from the group consisting of H, $C_1$–$C_6$ alkyl, halogen, —OH, —SH, —S($C_1$–$C_6$ alkyl), —CN, $C_1$–$C_6$ alkoxy, $C_1$–$C_6$ alkylcarboxy, $CF_3$, —$NO_2$, —$NH_2$, $(C_1$–$C_6)$ alkylamino, phenyl, $(C_1$–$C_6)$-alkoxycarbonyl and $R^7$-phenoxy, or adjacent ring carbon atoms form a ring with the group —$O(CH_2)_{1-2}O$—, —$O(CH_2)_{2-3}$— or —$O(CF_2)O$—;
$R^7$ is 1–3 substituents independently selected from the group consisting of H, $C_1$–$C_6$ alkyl, halogen, —OH, $C_1$–$C_6$ alkoxy and $CF_3$;
$R^8$ is H, $C_1$–$C_6$ alkyl or $(C_1$–$C_4)$alkoxy-$(C_1$–$C_4)$alkyl;
$R^9$ is H, $C_1$–$C_6$ alkyl or aryl-$(C_1$–$C_4)$alkyl;
$R^{10}$ is independently selected from the group consisting of H, $C_1$–$C_6$ alkyl and aryl;
$R^{11}$ is

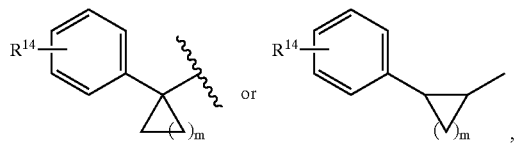

or, when $R^2$ is $R^6$-heteroaryl or $R^{10}$ is not H, $R^{11}$ can also be $R^5$-phenyl$(C_0$–$C_2)$alkyl;
m is 1, 2, 3, 4 or 5;
$R^{12}$ is H or $C_1$–$C_6$ alkyl;
$R^{13}$ is 1 to 3 substituents independently selected from the group consisting of H, $C_1$–$C_6$ alkyl, halogen, —OH, $C_1$–$C_6$ alkoxy, —$CF_3$, —$OCF_3$, —$NO_2$ and —$C(O)CH_3$; and
$R^{14}$ is 1–3 substituents independently selected from the group consisting of H, $C_1$–$C_6$ alkyl, halogen, —OH, $C_1$–$C_6$ alkoxy and $CF_3$.

The present invention also relates to a method of treating eating disorders, such as obesity and hyperphagia, and diabetes comprising administering to a mammal in need of such treatment an effective amount of a compound of formula I.

Another aspect of the invention is a pharmaceutical composition for treating eating disorders and diabetes which comprises a compound of formula I in combination with a pharmaceutically acceptable carrier.

DETAILED DESCRIPTION

Referring to formula I, above, one group of preferred compounds is that wherein W is $R^1$—$CR^3R^{12}NR^4C(O)$—.

$R^1$ is preferably $R^5$-phenyl, $R^5$ is preferably H, halogen, $C_1$-$C_6$ alkyl or phenyl, more preferably halogen or phenyl.

Another group of preferred compounds is that wherein $R^2$ is $R^6$-aryl, especially when n is 1. More preferred is $R^6$-aryl wherein "aryl" is phenyl and $R^6$ is 1–2 substituents.

X is preferably —$CHR^8$ wherein $R^8$ is H and Y is CH, or X and Y form a double bond.

$R^3$ is preferably ethyl or methyl, and $R^4$ and $R^{12}$ are each preferably H.

$R^{10}$ is preferably H or —$CH_3$; when n is 2–5, preferably only one $R^{10}$ is alkyl and the rest are hydrogen.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

"Alkyl" represents a straight or branched saturated hydrocarbon chain having the designated number of carbon atoms. Where the number of carbon atoms is not specified, 1 to 6 carbons are intended.

"Cycloalkyl" represents a saturated carbocyclic ring having 3 to 8 carbon atoms.

The term "heterocycloalkyl" refers to 4- to 7-membered saturated rings comprising 1 to 3 heteroatoms independently selected from the group consisting of —O—, —S— and —$NR^7$—, wherein $R^7$ is H or $C_1$-$C_6$ alkyl, and wherein the remaining ring members are carbon. Where a heterocyclic ring comprises more than one heteroatom, no rings are formed where there are adjacent oxygen atoms, adjacent sulfur atoms, or three consecutive heteroatoms. Examples of heterocyclic rings are tetrahydrofuranyl, pyrrolidinyl, tetrahydropyranyl, piperidinyl, morpholinyl, thiomorpholinyl and piperazinyl.

Halogen represents fluoro, chloro, bromo or iodo.

Aryl represents a monoaromatic ring or a bicyclic fused ring system of 6- to 10 carbon atoms, possessing one or two aromatic rings including, but not limited to, phenyl, naphthyl, tetrahydronaphthyl, indanyl, and the like.

Heteroaryl means a 5- to 10-membered single or benzofused aromatic ring comprising 1 to 3 heteroatoms independently selected from the group consisting of —O—, —S— and —N=, provided that the rings do not include adjacent oxygen and/or sulfur atoms. Examples of single ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused rings are indolyl, benzofuranyl, quinolyl, quinazolinyl, quinoxalinyl, benzoxazolyl, benzothiazolyl, benzothiadiazolyl, thianaphthenyl, and benzofurazanyl. N-oxides are also included. All positional isomers are contemplated, e.g., 2-pyridyl, 3-pyridyl and 4-pyridyl.

When a variable appears more than once in the structural formula, for example $R^5$, the identity of each variable appearing more than once may be independently selected from the definition for that variable.

N-oxides can form on a tertiary nitrogen present in an $R^1$ or $R^2$ substituent, or on =N— in a heteroaryl ring substituent and are included in the compounds of formula I.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I. The preferred stereochemistry for compounds of the invention wherein W is $R^1$—$CR^3R^{12}NR^4C(O)$— is shown in formula IA:

IA

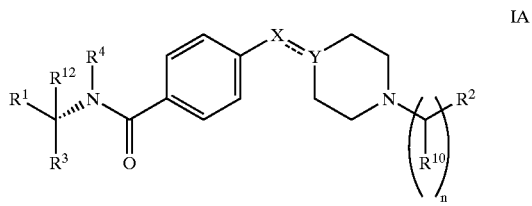

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I can be produced by processes known to those skilled in the art using either solution phase or solid phase synthesis as shown in the following reaction schemes and in the preparations and examples below:

Compounds of Formula 1 wherein W is $R^1$—$CR^3R^{12}NR^4C(O)$— can be produced as shown in Scheme 1.

Scheme 1

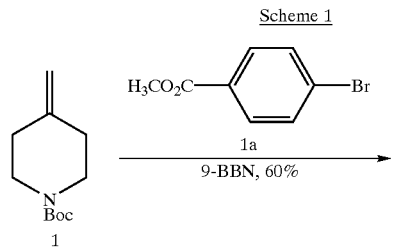

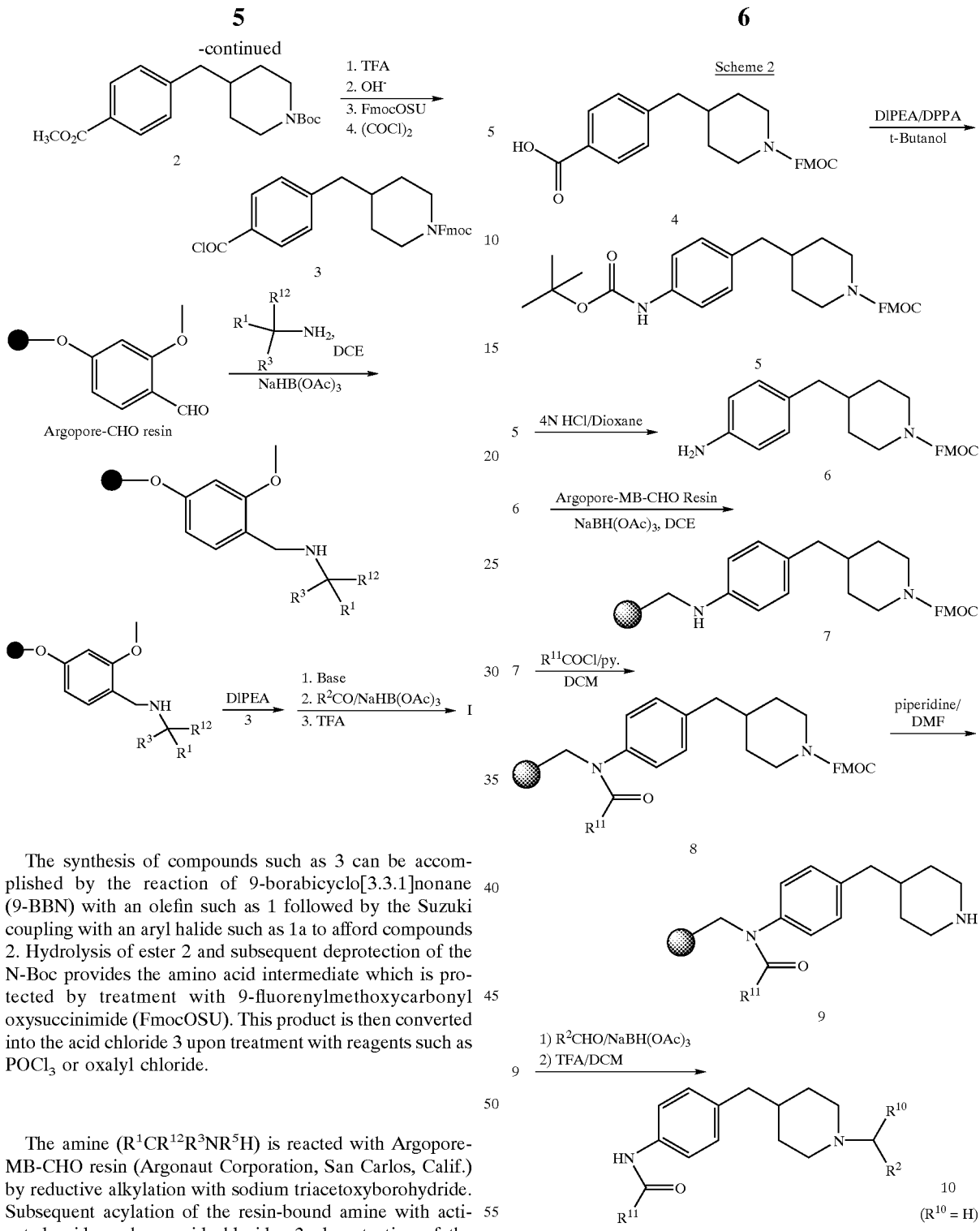

The synthesis of compounds such as 3 can be accomplished by the reaction of 9-borabicyclo[3.3.1]nonane (9-BBN) with an olefin such as 1 followed by the Suzuki coupling with an aryl halide such as 1a to afford compounds 2. Hydrolysis of ester 2 and subsequent deprotection of the N-Boc provides the amino acid intermediate which is protected by treatment with 9-fluorenylmethoxycarbonyl oxysuccinimide (FmocOSU). This product is then converted into the acid chloride 3 upon treatment with reagents such as $POCl_3$ or oxalyl chloride.

The amine ($R^1CR^{12}R^3NR^5H$) is reacted with Argopore-MB-CHO resin (Argonaut Corporation, San Carlos, Calif.) by reductive alkylation with sodium triacetoxyborohydride. Subsequent acylation of the resin-bound amine with activated acids such as acid chlorides 3, deprotection of the N-Fmoc group, followed by reductive alkylation with aldehydes or ketones, or reaction with an aldehyde followed by treatment with a Grignard reagent, or by reaction with the appropriate mesylate or alkyl halide, provides a resin bound intermediate, which on treatment with trifluoroacetic acid (TFA) produces compounds of Formula I.

Compounds of Formula 1 wherein W is $R^{11}C(O)NR^4$ can be prepared according to Scheme 2.

Compounds 10 can be prepared by the route shown in Scheme 2 by first converting an acid such as 4 into an amine such as 6 by the Curtius reaction, for example by treatment with diphenylphosphoryl azide in an alcohol such as t-butanol followed by hydrolysis. Subsequent reaction with a resin-bound aldehyde such as the Argopore MB-CHO resin under reducing conditions provides a resin-bound amine 7 which can be further functionalized by reaction with activated carboxylic acid derivatives such as acid chlorides.

Removal of the FMOC group and reductive alkylation with carbonyl-containing compounds, followed by treatment with acid to remove the compound from the polymeric resin, provides compounds 10.

Alternatively, compounds of formula I are prepared as shown in Scheme 3 by reacting an aryl bromide such as 11a with an alkyl lithium reagent, followed by addition of an aryl isocyanate. Subsequent removal of the BOC group from compound 12 by treatment with acid and then introduction of the $R^2$ group by alkylation or reductive alkylation provides compounds such as 13. Furthermore, 11 can also be elaborated into compounds such as 11i as shown in Scheme 3.

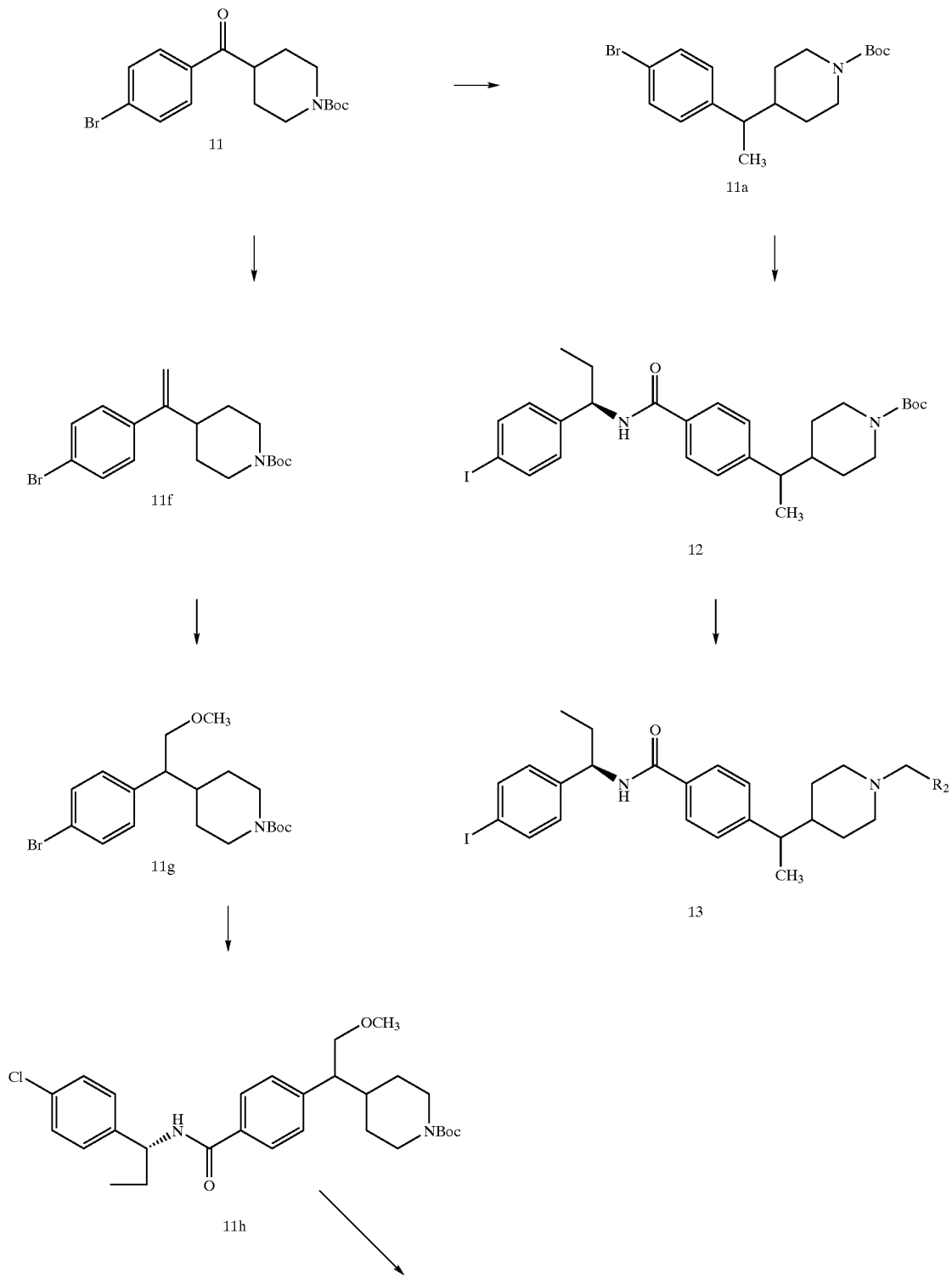

Scheme 3

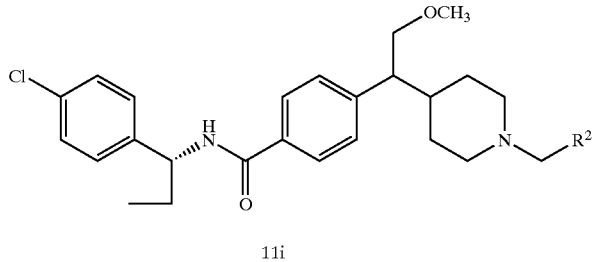
11i
Compounds wherein $R^{10}$ is alkyl can be prepared by the following procedure:
Scheme 4
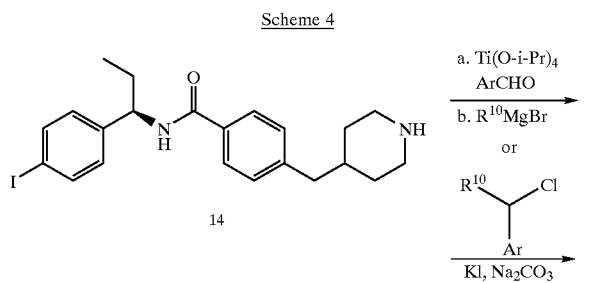
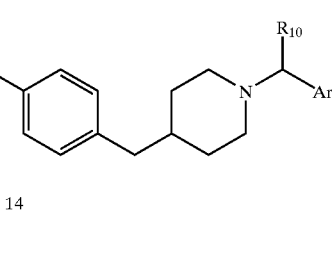
14
Additional compounds of formula I are prepared according the route shown in Scheme 5 (specific compounds are shown, but the procedure may be modified to make other compounds within the scope of formula I):
Scheme 5
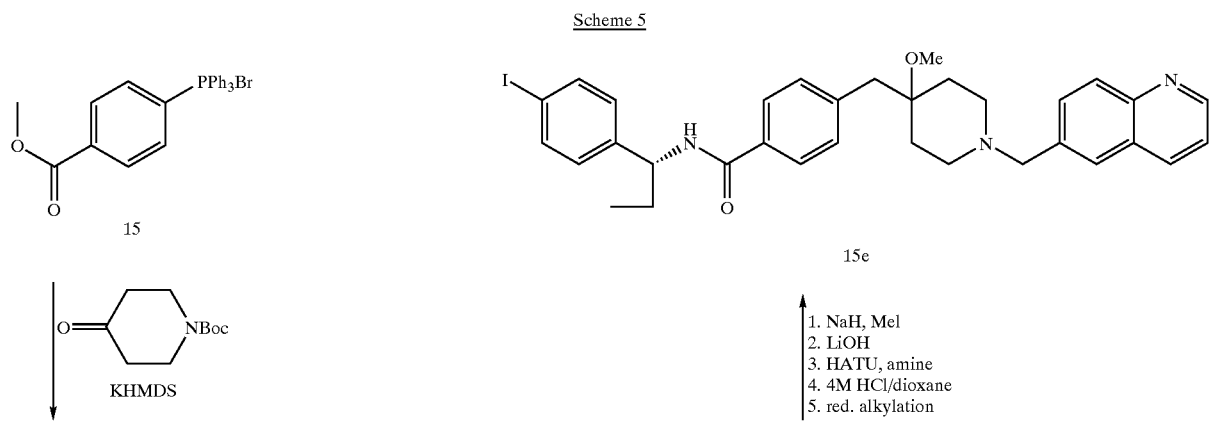
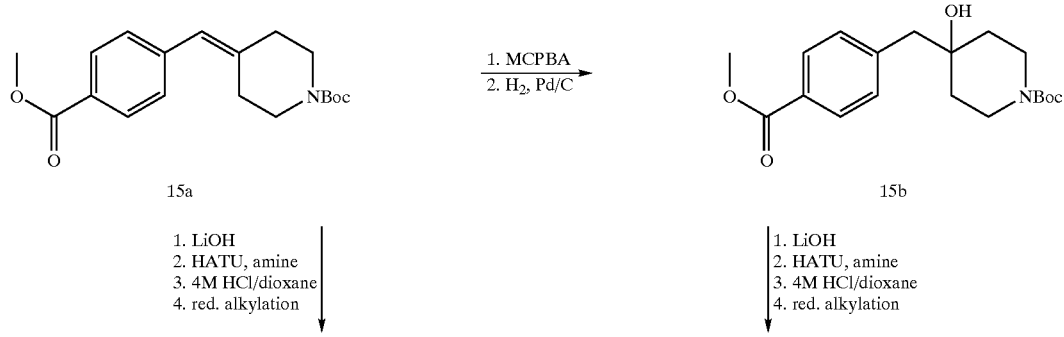

-continued

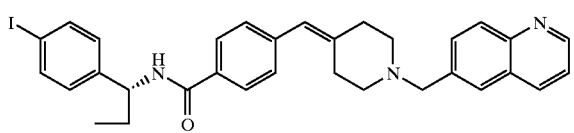

15d

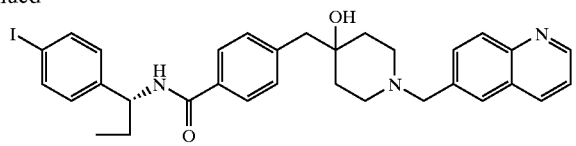

15c

Compounds of formula I wherein W is R¹—CR³R¹²NR⁴C(O)— and R¹ is biphenyl can be prepared by the Suzuki coupling reaction:

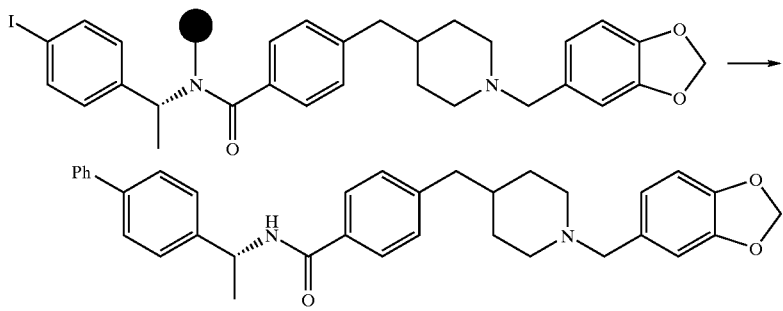

The iodophenyl analogs on Argopore-MB-CHO resin are treated with phenylboronic acid, $K_2CO_3$, Pd(dppf)Cl$_2$ and 1-methyl-2-pyrrolidinone. The resin is washed, then cleaved using 10% TFA/CH$_2$Cl$_2$.

Starting materials are prepared by known methods and/or methods described in the Preparations.

The compounds of formula I exhibit MCH receptor antagonizing activity, which has been correlated with pharmaceutical activity for treating eating disorders, such as obesity and hyperphagia, and diabetes.

The compounds of formula I display pharmacological activity in a test procedure designed to demonstrate MCH receptor antagonist activity. The compounds are non-toxic at pharmaceutically therapeutic doses. Following is a description of the test procedure.

MCH Receptor Binding Assay

Membranes from CHO cells expressing the MCH receptor were prepared by lysing cells with 5 mM HEPES for 15 min at 4 C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM MGCl$_2$, 10 mM NaCl, 5 mM MnCl$_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 l) was then added to 96-well plates containing 50 l of 500 pM [$^{125}$I]-MCH (NEN) and 50 ml of the appropriate concentration of compound (4× the desired final concentration). Nonspecific binding was determined by including 1 M MCH in the binding reaction. The binding reaction was incubated at room temperature for 2 h. Plates were then analyzed in a TOPCOUNT microplate scintillation counter (Packard). Data was analyzed and Ki values were determined using GraphPad Prim.

For the compounds of this invention, a range of MCH receptor binding activity (Ki values) of from about 3 nM to about 1500 nM was observed. Compounds of this invention preferably have a binding activity in the range of from about 3 nM to about 500 nM, more preferably from about 3 to about 200 nM, and most preferably from about 3 to about 80 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The invention disclosed herein is exemplified by the following preparations and examples which should not be construed to limit the scope of the disclosure. Alternative mechanistic pathways and analogous structures may be apparent to those skilled in the art. The following terms are abbreviated: room temperature (rt); ethyl acetate (EtOAc); tetrahydrofuran (THF); dimethylformamide (DMF); diisopropylethylamine (DIPEA); and dichloroethane (EDC).

Preparation 1

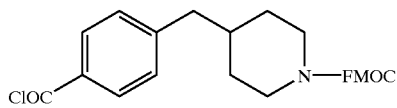

See Scheme 1, above.

Mix starting material 1 (1 g) with 9-BBN (10.2 ml of a 0.5 M THF solution), place under a $N_2$ atmosphere and heat to reflux for 1 h. To the cooled solution add methyl 4-bromobenzoate (1.09 g), $K_2CO_3$ (0.84 g), $PdCl_2(dppf)$ (0.21 g), $Ph_3As$ (0.155 g), DMF (7 ml) and water (1.1 ml) and heat at 65° C. for 3 h. Pour the reaction mixture into ice water, extract into EtOAc and purify the organic layer by flash chromatography (Hex: EtOAc (90:10) to yield compound 2 (1.1 g). Dissolve compound 2 (1.1 g) in $CH_3OH$ (20 ml) and add LiOH (0.2 g) and water (7.5 ml). After heating to reflux for 1 h, cool the reaction mix, remove the $CH_3OH$ under vacuum and acidify the mixture with HCl. Collect the solid by filtration and dry in vacuo, and dissolve in 4 M HCl in dioxane (35 ml) and stir for 1.5 h. Add ether and collect the solid (0.67 g) by filtration. Add the solid (0.66 g) to a solution of $Na_2CO_3$ (0.6 g) in water (120 ml) and dioxane (40 ml) followed by dropwise addition at 0° C. of a solution prepared from FMOC-OSuc (0.87 g) and dioxane (10 ml). After 2 h at rt, remove the dioxane under vacuum and acidify the mixture with HCl. Collect the solid by filtration and dry in vacuo (0.93 g, LCMS 442.1[M+H]). Treat the residue with oxalyl chloride in $CH_2Cl_2$ to obtain the title compound.

Preparation 2

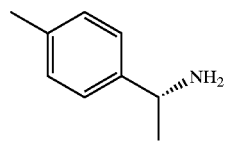

Step 1:

To a solution of (R)-α-methylbenzylamine (7.0 g, 57.8 mmol, 1 eq )/10 ml EDC was added trifluoroacetic anhydride (10 ml, 1.22 eq) in EDC (10 ml) below 30° C. The mixture was stirred for 1.5 h and then cooled to 0° C. Iodine (7.0 g, 0.48 eq) was added, followed by addition of bis (trifluoroacetoxy)iodobenzene (12.6 g, 0.5 eq). The mixture was stirred overnight and quenched by 10% $Na_2S_2O_3$ (130 ml). 130 ml $CH_2Cl_2$ was added and the organic layer was washed with saturated $NaHCO_3$. After drying over $Na_2CO_3$ and removing $CH_2Cl_2$, the solid was dissolved in ether (50 ml) by heat, followed by addition of hexane (150 ml). White solids were precipitated out and the mixture was further stirred for 2 h. Filtration afforded white crystal, which was washed with hexane (30 ml×2) and air-dried. 9.2 g of the desired product was obtained in 46% yield. $^1$HNMR ($CDCl_3$): δ 1.6 (d, 3H, J=7.3 Hz), 5.08 (m, 1H), 6.40 (br s, 1H), 7.05 (d, 2H, J=8.3 Hz), 7.70 (d, 2H, J=8.3 Hz).

Step 2:

The product of step 1 (1 g, 2.91 mmol, 1 eq) was dissolved in $CH_3OH$ (35 ml), water (10 ml) and 2N NaOH (6 ml). The solution was stirred overnight and TLC showed complete conversion. The solvent was removed and extraction with $CH_2Cl_2$ several times provided the desired product as colorless oil (0.69 g, 96% yield).

$^1$HNMR ($CDCl_3$): δ 1.22 (d, 3H, J=6.5 Hz), 1.40 (s, 2H), 3.98 (q, 1H, J=6.6 Hz), 7.00 (d, 2H, J=8.3 Hz)), 7.58 (d, 2H, J=8.3 Hz). $^{13}$CNMR ($CDCl_3$): δ 27.12, 51.98, 93.09, 128.92, 138.36, 148.38. HRMS for $C_8H_{11}IN$ (M+1) calcd: 247.9936; found: 247.9936.

Preparation 3

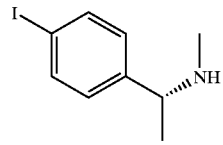

To a solution of the product of Preparation 2, step 1, (1 g, 2.92 mmol, 1 eq)/10 ml THF at 0° C. under $N_2$ was added KHMDS (0.5 M in toluene, 7 ml, 1.2 eq) dropwise. 20 min later, $CH_3I$ (0.36 ml, 2 eq) was added and the mixture was stirred overnight. After workup and flash chromatography (EtOAc:hexane, 1:10), 1 g of the desired product was obtained. 2:1 rotamers were observed, the major one was reported as:

$^1$HNMR ($CDCl_3$): δ 1.58 (d, 3H, J=6.6 Hz), 2.80 (s, 3H), 5.90 (q, 1H, J=6.6 Hz), 7.00 (d, 2H, J=8.3 Hz), 7.75 (d, 2H, J=8.3 Hz).

The above product was hydrolyzed in $NaOH/CH_3OH$ to the amine in 85% yield. $^1$HNMR ($CDCl_3$: δ 1.30 (d, 3H, J=6.6 Hz), 1.40 (br s, 1H), 2.30 (s, 3H), 3.60 (q, 1H, J=6.6 Hz), 7.05 (d, 2H, J=8.3 Hz), 7.61 (d, 2H, J=8.3 Hz).

Preparation 4

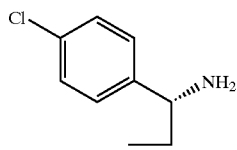

4'-Chloropropiophenone was reduced to (S)-4-chloro-α-ethylbenzyl alcohol according to *J. Org. Chem.* (1993), 58, 2880–2888. (>95% ee by NMR of the corresponding Mosher's esters.)

¹HNMR (CDCl₃): δ 0.98 (t, 3H, J=7.4 Hz), 1.60–1.78 (m, 2H), 1.80–2.00 (br s, 1H), 4.58 (t, 1H, J=6.7 Hz), 7.22 (d, 2H, J=8.4 Hz), 7.30 (d, 2H, J=8.4 Hz).

The (S)-4-chloro-α-ethylbenzyl alcohol was then converted to the corresponding (R)-azide according to *J. Org. Chem.* (1993), 58, 2880–2888.

¹HNMR (CDCl₃): δ 0.98 (t, 3H, J=7.4 Hz), 1.70–1.85 (m, 2H), 4.35 (t, 1H, J=6.7 Hz), 7.22 (d, 2H, J=8.4 Hz), 7.38 (d, 2H, J=8.4 Hz).

The azide was reduced by triphenylphosphine to the amine by literature procedures (*J. Med. Chem.* (1997), 2755–61).

¹HNMR (CDCl₃): δ 0.98 (t, 3H, J=7.3 Hz), 1.60 (m, 2H), 3.75 (m, 1H) 7.20 (m, 4H). ¹³CNMR (CDCl₃): δ 12.08, 33.64, 58.35, 128.83, 129.43, 132.97, 133.33.

Preparation 5

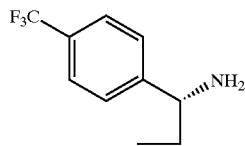

(R)-α-ethyl-4-trifluoromethylbenzylamine was prepared by methods similar to the above procedures. ¹HNMR (CDCl₃): δ 0.90 (t, 3H, J=7.4 Hz), 1.60–1.78 (m, 2H), 2.00–2.18 (brs), 3.90 (t, 1H, J=6.9 Hz), 7.41 (d, 2H, J=8.2 Hz), 7.60 (d, 2H, J=8.2 Hz).

Preparation 6

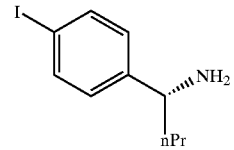

The title compound was prepared by a procedure similar to that described above. ¹HNMR (CDCl₃): δ 0.99 (t, 3H, J=7.3 Hz), 1.20–1.40 (m, 2H), 1.50–1.70 (m, 4H), 3.92 (t, 1H, J=6.9 Hz), 7.10 (d, 2H, J=8.3 Hz), 7.60 (d, 2H, J=8.3 Hz).

Preparation 7

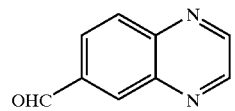

6-Methylquinoxaline was oxidized by SeO₂ to 6-formylquinoxaoline in >80% yield according to Chem. Abstr. (1945), 39, 4077–4078.

¹HNMR (CDCl₃): δ 8.20 (m, 2H), 8.59 (s, 1H), 8.98 (s, 1H), 10.22 (s, 1H).

Preparation 8

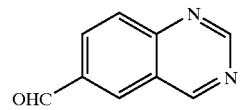

6-Methylquinazoline (prepared from 4-hydroxy-6-methylquinazoline according to *J. Am. Chem. Soc.* (1962) 561) was oxidized by SeO₂ to 6-formylquinazoline in 10% yield. ¹HNMR (CDCl₃): δ 8.20 (d, 1H, J=8.3 Hz), 8.40 (d, 1H, J=8.3 Hz), 8.45 (s, 1H), 9.40 (s, 1H), 9.50 (s, 1H), 10.20 (s, 1H).

Preparation 9

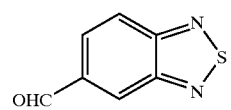

5-Methyl-2,1,3-benzothiadiazole was converted to the corresponding aldehyde according to the procedure of *Eur. J. Med. Chem.* (1993), 28, 141.

¹HNMR (CDCL₃) δ 8.10 (s, 2H), 8.50 (s, 1H), 10.20 (s, 1H).

EXAMPLE 1

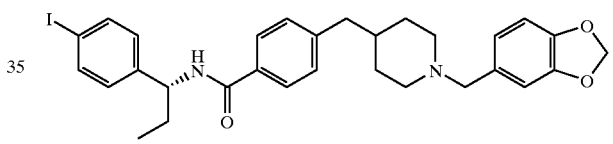

Step 1:

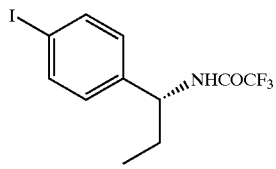

To (R)-α-ethylbenzylamine (19.8 g, 146.7 mmol, 1 eq) in EDC (30 ml) at 0° C. was added trifluoroacetic anhydride (25.3 ml, 1.22 eq) dropwise. The ice bath was removed and the mixture was stirred for 1.5 h. The crude was then cooled to 0° C. followed by the addition of 12 (17.9 g, 0.48 eq) and bis(trifluoroacetoxy)iodobenzene (32.1 g, 0.51 eq). The dark purple mixture was stirred for 18 h until it became slightly yellow. 10% Na₂S₂O₃ (330 ml) and CH₂Cl₂ (330 ml) were added and stirred at 0° C. for 0.5 h. After separation, the organic layer was washed with saturated NaHCO₃ until the pH of the aqueous layer was 9. After further extraction with CH₂Cl₂, the organic layers were combined and dried over Na₂CO₃. Removal of the solvent provided a white solid which was redissolved in CH₂Cl₂ (300 ml). The solution was treated with 1 liter of hexane and white solid precipitated. After filtration and washing with hexane and ether, 26.5 g of the desired product as white solid was obtained in 50% yield.

Step 2:

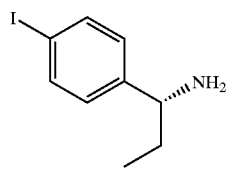

The product of Step 1 (25 g) was dissolved in CH$_3$OH (200 ml), treated with 3 N NaOH (100 ml) at 0° C. and gradually warmed up to rt overnight. The solvent was removed .and the solution was extracted with CH$_2$Cl$_2$ followed by drying with Na$_2$CO$_3$. After removal of the solvent, 14 g of the desired product was obtained in 77% yield.

$^1$HNMR (CDCl$_3$): δ 0.82 (d, 3H, J=7.3 Hz), 1.46 (s, 2H), 1.60 (m, 2H), 3.78 (t, 1H, J=6.7 Hz), 7.05 (d, 2H, J=8.3 Hz), 7.60 (d, 2H, J=8.3 Hz). $^{13}$CNMR (CDCl$_3$): δ 12.14, 33.60, 58.46, 93.10, 129.56, 138.35, 146.99. HRMS for C$_9$H$_{13}$IN (M+1) calcd: 262.0093; found: 262.0092. Elemental analysis: C, H, N. N: calcd: 5.36; found: 4.60.

Step 3:

The Argopore aldehyde resin (Argonaut Corporation, San Carlos, Calif.) (10 g, 0.76 mmol/g) in EDC (40 ml) was stirred with the product of Step 2 (7.93 g, 4 eq) for 15 min followed by addition of NaB(OAc)$_3$H (6 g, 4 eq). The mixture was stirred under N$_2$ at rt for 20 h before being quenched with CH$_3$OH. The CH$_3$OH was removed and the crude was treated with 2N NH$_3$/CH$_3$OH for 0.5 h. The resin was further washed with CH$_3$OH, CH$_2$Cl$_2$ (3 times each) and dried under vacuum at 40° C. overnight.

Step 4:

The resin from Step 3 was treated with 10 eq of DIPEA and 2 eq of the product of Preparation 1 in CH$_2$Cl$_2$ at rt overnight. The resin was then washed with CH$_2$Cl$_2$ several times.

Step 5:

The resin of Step 4 was treated with 20% piperidine/DMF for 1 h (twice). After washing with CH$_2$Cl$_2$, then EDC, the resin was treated with EDC, piperonal (10 eq) and NaB (OAc)$_3$H (10 eq) under N$_2$ for 24–48 h. The resin was then washed with CH$_3$OH, 2N NH$_3$/CH$_3$OH, CH$_3$OH, CH$_2$Cl$_2$ (3 times each) and dried under vacuum. Final cleavage was done with 10% TFA/CH$_2$Cl$_2$ (1 h). The crude (TFA salt) was chromatographed to give the title compound (Rf=0.45, CH$_2$Cl$_2$/CH$_3$OH/NH$_4$OH=97/3/1).

$^1$H NMR(CDCl$_3$): δ 0.99 (t, 3H, J=7.3 Hz), 1.22–1.37 (m, 2H), 1.45–1.60 (m, 3H), 1.80–1.99 (m, 4H), 2.58 (d, 2H, J=6.6 Hz), 2.82 (d, 2H, J=7.4 Hz), 3.40 (s, 2H), 5.00 (q, 1H, J=7.4 Hz), 5.90 (s, 2H), 6.25 (d, 1H, J=8.0 Hz), 6.70 (s, 2H), 6.80 (s, 1H), 7.10 (d, 2H, J=8.0 Hz), 7.18 (d, 2H, J=8.0 Hz), 7.65 (d, 4H, J=8.1 Hz). MS for C$_{30}$H$_{33}$IN$_2$O$_3$: 597 (M+1)$^+$; Tr=6.7 min (gradient A (CH$_3$CN)/B (water with 0.1% TFA): from 5% A/B to 95% A/B in 10 min.)

Using a similar procedure with the appropriate amines and aldehydes, the following compounds of formula I were prepared, wherein R$^1$—CR$^{12}$R$^3$— and

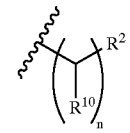

are as defined in the following Table 1:

| Ex. | R$^1$—CR$^{12}$R$^3$— | ![structure] | Rt (min.) | Obs. Mass |
|---|---|---|---|---|
| 1-1 | (1-phenylethyl) | (2,4-dimethylbenzyl) | 6.06 | 441.1 |
| 1-2 | (1-phenylethyl) | (1-methyl-2-phenylethyl) | 5.96 | 441.1 |

-continued
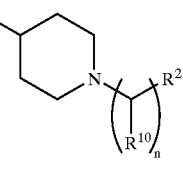
| Ex. | R¹—CR¹²R³— | 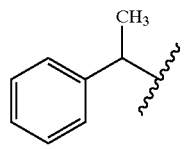 | Rt (min.) | Obs. Mass |
|---|---|---|---|---|
| 1-3 | 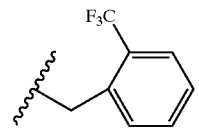 | 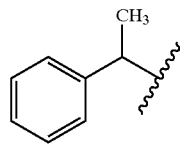 | 5.96 | 481.1 |
| 1-4 | 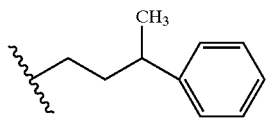 | 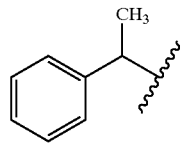 | 6.21 | 455.1 |
| 1-5 | 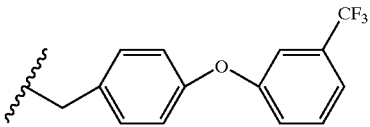 | 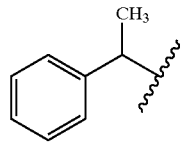 | 7.06 | 573.1 |
| 1-6 | 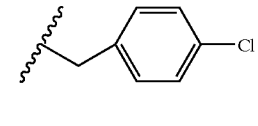 | 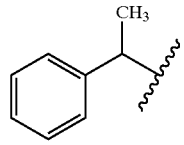 | 5.86 | 447.1 |
| 1-7 | 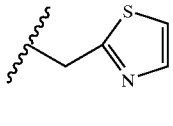 | 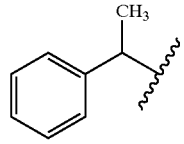 | 4.91 | 420.1 |
| 1-8 | 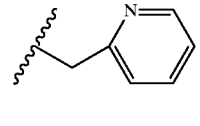 | 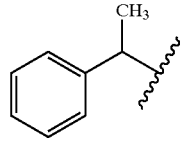 | 5.01 | 414.1 |
| 1-9 | 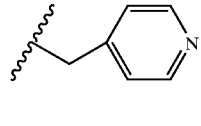 | 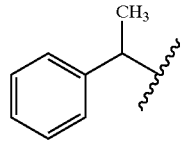 | 4.26 | 414.1 |
| 1-10 | 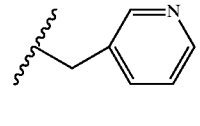 | | 4.36 | 414.1 |

-continued
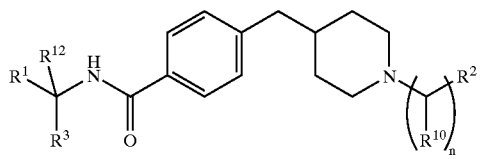
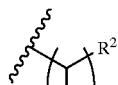
| Ex. | R¹—CR¹²R³— | (wavy)-R²/(R¹⁰)ₙ | Rt (min.) | Obs. Mass |
|---|---|---|---|---|
| 1-11 | 1-phenylethyl | 4-isopropylbenzyl | 6.41 | 455.1 |
| 1-12 | 1-phenylethyl | 4-bromobenzyl | 5.96 | 493.1 |
| 1-13 | 1-phenylethyl | 4-trifluoromethylbenzyl | 6.16 | 481.1 |
| 1-14 | 1-phenylethyl | 2,3-dichlorobenzyl | 6.01 | 481.1 |
| 1-15 | 1-(4-bromophenyl)ethyl | 4-methylthiobenzyl | 4.66 | 537 |
| 1-16 | 1-(4-bromophenyl)ethyl | 3,4-methylenedioxybenzyl | 6.71 | 537 |
| 1-17 | 1-(4-iodophenyl)ethyl | 3,4-methylenedioxybenzyl | 4.51 | 583 |
| 1-18 | 1-(2-naphthyl)ethyl | 2,4-dimethylbenzyl | 7.31 | 491 |

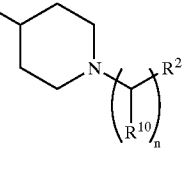

-continued
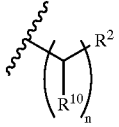
| Ex. | R¹—CR¹²R³— | 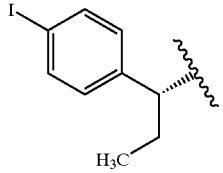 | Rt (min.) | Obs. Mass |
|---|---|---|---|---|
| 1-25 | 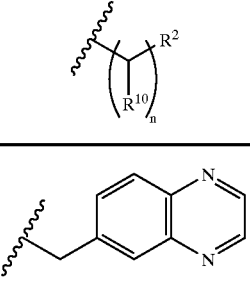 | 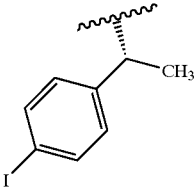 | 5.21 | 605.1 |
| 1-26 | 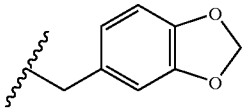 | 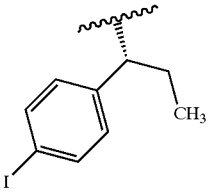 | 4.51 | 583.1 |
| 1-27 | 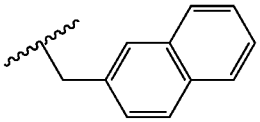 | 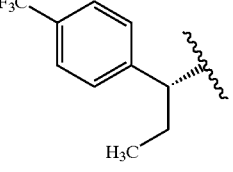 | 8.46 | 603.1 |
| 1-28 | 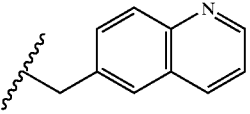 | 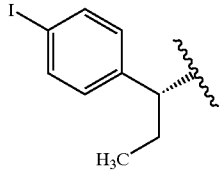 | 7.46 | 546 |
| 1-29 | 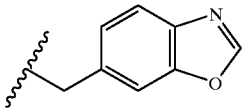 | 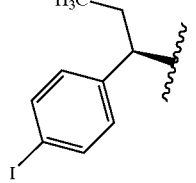 | 5.16 | 594 |
| 1-30 | 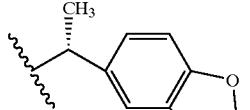 | | 5.01 | 611 |

-continued
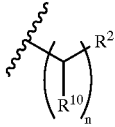
| Ex. | R¹—CR¹²R³— | 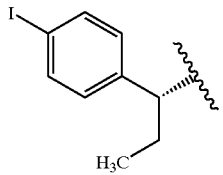 | Rt (min.) | Obs. Mass |
|---|---|---|---|---|
| 1-31 | 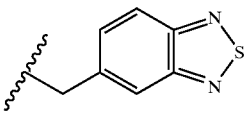 | 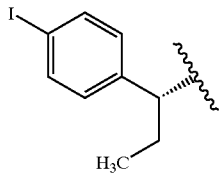 | 5.31 | 611.1 |
| 1-32 | 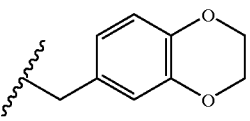 | 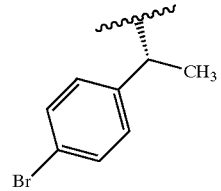 | 8.61 | 611.1 |
| 1-33 | 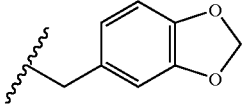 | 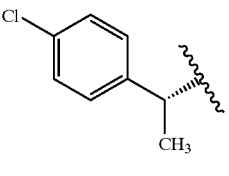 | 6.66 | 535.1 |
| 1-34 | 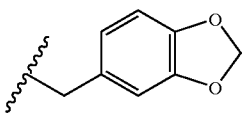 | 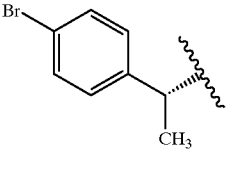 | 4.91 | 491 |
| 1-35 | 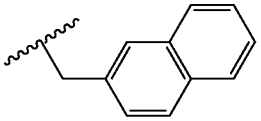 | 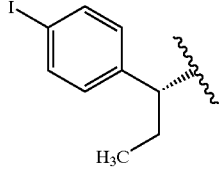 | 4.71 | 541 |
| 1-36 | 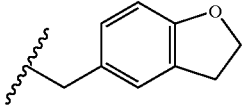 |  | 4.31 | 595 |

-continued

| Ex. | $R^1$—$CR^{12}R^3$— | (R²/R¹⁰ₙ group) | Rt (min.) | Obs. Mass |
|---|---|---|---|---|
| 1-37 | 4-I-C₆H₄-CH(CH₂CH₂CH₃)— | methylenedioxyphenyl-CH₂— | 5.36 | 611 |
| 1-38 | 4-Br-C₆H₄-CH(CH₃)— | 2-ethyl-4-methylphenyl-CH₂— | 7.21 | 519 |
| 1-39 | 4-Br-C₆H₄-CH(CH₃)— | 4-Br-C₆H₄-CH₂— | 4.51 | 571 |
| 1-40 | 4-(CH₃OC(O))-C₆H₄-CH(CH₂CH₃)— | methylenedioxyphenyl-CH₂— | 7.26 | 529 |
| 1-41 | 4-Br-C₆H₄-CH(CH₃)— | 4-OCH₃-naphthyl-CH₂— | 4.71 | 571 |
| 1-42 | 4-I-C₆H₄-CH(CH₂CH₃)— | 4-Cl-C₆H₄-CH₂— | 8.26 | 587 |

-continued

| Ex. | R¹—CR¹²R³— | (R²/R¹⁰)ₙ structure | Rt (min.) | Obs. Mass |
|---|---|---|---|---|
| 1-43 | 4-Br-C₆H₄-CH(CH₃)- | 3-CH₃-4-OCH₃-C₆H₃-CH₂- | 4.66 | 535.1 |
| 1-44 | 4-H₃CO-C₆H₄-CH(CH₃)- | 3,4-methylenedioxybenzyl | 4.61 | 487 |
| 1-45 | 4-Br-C₆H₄-CH(CH₃)- | 4-OCH₃-C₆H₄-CH₂- | 6.81 | 521.1 |
| 1-46 | 4-Br-C₆H₄-CH(CH₃)- | 4-CH₃-naphthalen-1-yl-CH₂- | 4.86 | 555 |
| 1-47 | 4-Br-C₆H₄-CH(CH₃)- | 2,4-di-CH₃-C₆H₃-CH₂- | 4.65 | 519 |

-continued
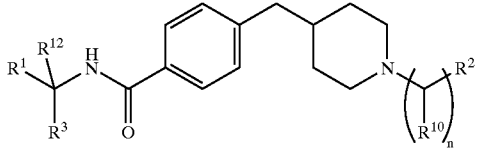
| Ex. | R¹—CR¹²R³— | 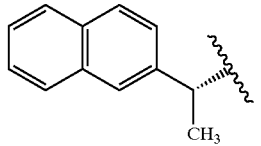 | Rt (min.) | Obs. Mass |
|---|---|---|---|---|
| 1-48 | 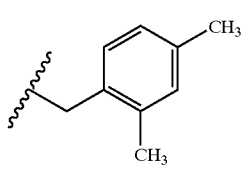 | 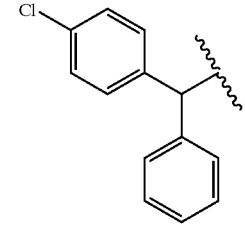 | 7.31 | 491 |
| 1-49 | 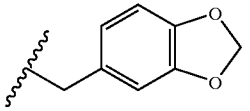 | 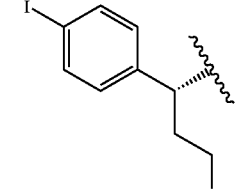 | 5.31 | 553 |
| 1-50 | 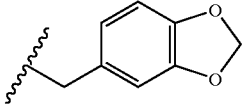 | 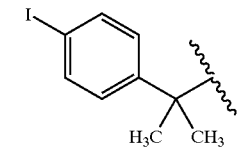 | 5.36 | 611 |
| 1-51 | 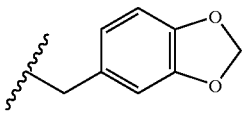 | 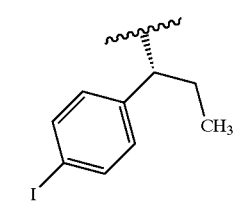 | 5.21 | 597 |
| 1-52 | 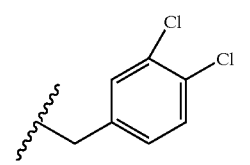 | 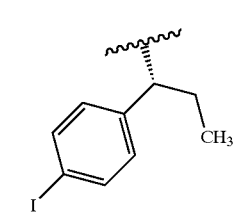 | 8.51 | 621 |
| 1-53 | 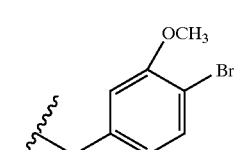 |  | 8.11 | 663 |

-continued

| Ex. | R¹—CR¹²R³— | (R² / R¹⁰ₙ group) | Rt (min.) | Obs. Mass |
|---|---|---|---|---|
| 1-54 | 4-iodophenyl-CH(CH₃)— | 2,2-difluoro-benzodioxol-5-yl-CH₂— | 8.41 | 633 |
| 1-55 | 3-methoxyphenyl-CH(CH₃)— | benzo[1,3]dioxol-5-yl-CH₂— | 4.85 | 487 |
| 1-56 | 4-methoxyphenyl-CH(CH₃)— | benzo[1,3]dioxol-5-yl-CH₂— | 4.82 | 487 |

EXAMPLE 2

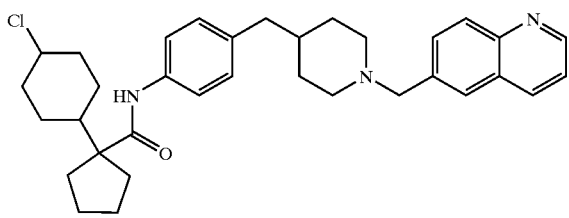

Step 1:

The acid 4 (4.42 g, 0.01 mol) is suspended in distilled t-butanol (30 ml), DIPEA (1.66 ml, 0.0095 mol) and diphenylphosphoryl azide (2.16 ml, 0.01 mol) are added under $N_2$, and the mixture is refluxed overnight. The t-butanol is removed by rotoevaporation, and the concentrated residue is purified by flash chromatography (EtOAc/Hexane (1:3) with 10% $CH_2Cl_2$), to obtain compound 5 (1.65 gm).

Step 2:

Compound 5 (2.85 g) is dissolved in 4N HCl in dioxane and stirred overnight, and concentrated. The residue is dissolved in 1N HCl, extracted with ether, and the HCl layer is basified with saturated $NaHCO_3$ solution to pH 9, and extracted with $CH_2Cl_2$ twice. The combined $CH_2Cl_2$ layer is washed with brine and dried over anhydrous $Na_2SO_4$, to give 6 (1.67 gm).

Step 3:

Argopore-MB-CHO resin (5.0 g, 0.76 mmol/g) is suspended in EDC (40 ml), amine 6 (1.67 g, 4.05 mmol) and $NaBH(OAc)_3$ (4.24 g, 20.25 mmol) is added and shaken for 70 h. $CH_3OH$ is added, the reaction stirred for 30 min., then the resin is washed with 2N $NH_3/CH_3OH$ (2×), $CH_3OH$ (2×), THF (2×) and $CH_2Cl_2$ (2×), and dried under vacuum to obtain resin 7.

Step 4:

Resin 7 (70 mg, 0.76 mmol/g) is suspended in anhydrous $CH_2Cl_2$, then anhydrous pyridine (0.045 ml, 0.532 mmol) is added and mixed, followed by addition of 1-(4-chlorophenyl) 1-cycylopentanecarbonyl chloride (65 mg, 0.266 mmol). The mixture is shaken is overnight, then washed with $CH_3OH$ (2×), THF (2×), $CH_2Cl_2$ (2×), and dried in vacuum to obtain resin bound amide. This resin is treated with 20% piperidine in DMF (3 times, 20 min each) then washed with THF (2×), $CH_3OH$ (2×), $CH_2Cl_2$ (2×), and dried. The resultant resin is suspended in EDC, 6-quinoline carboxaldehyde (167 mg, 1.06 mmol) and $NaBH(OAc)_3$ (112.8 mg, 0.532 mmol) are added and the mixture is shaken for 70 h. The resin is washed with THF (2×), $CH_3OH$ (2×), $CH_2Cl_2$ (2×), and treated with 40% $TFA/CH_2Cl_2$ for 30 min. The mixture is filtered and the volatiles are evaporated to obtain the title compound. LCMS Rt 7.69 min., observed mass 538.1 (M+H).

Using the same procedures with the appropriate acid chlorides and aldehydes the following compounds in Table 2 are obtained:
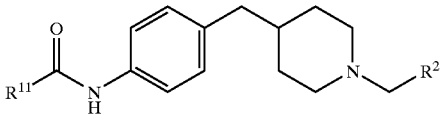
| Ex. | R[11] | R[2] | R$_t$ (min.) | Obs. Mass |
|---|---|---|---|---|
| 2-1 | 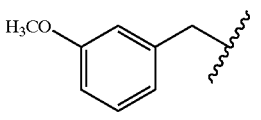 | 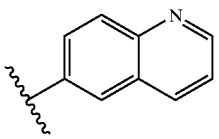 | 6.54 | 480.1 |
| 2-2 | 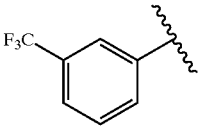 | 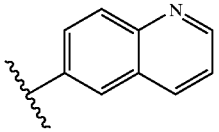 | 7.21 | 504.1 |
| 2-3 | 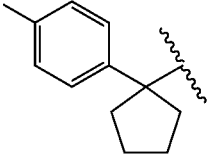 | 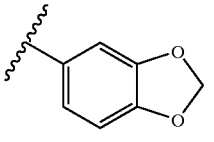 | 8.76 | 531.1 |
| 2-4 | 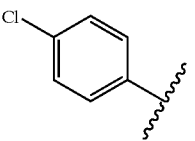 | 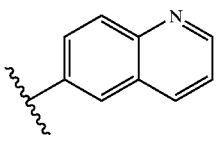 | 6.89 | 470.1 |
| 2-5 | 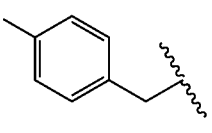 | 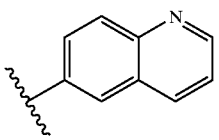 | 7.21 | 484.1 |
| 2-6 | 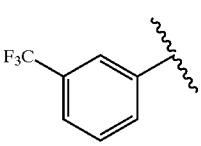 | 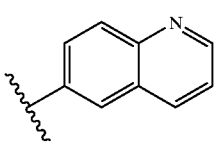 | 7.51 | 504.1 |
| 2-7 | 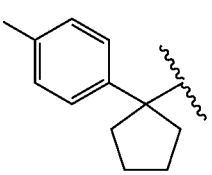 | 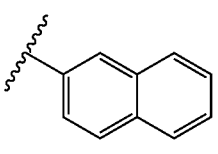 | 9.09 | 537.1 |
| 2-8 | 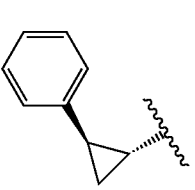 | 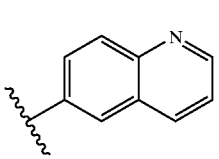 | 7.29 | 476.1 |

EXAMPLE 3

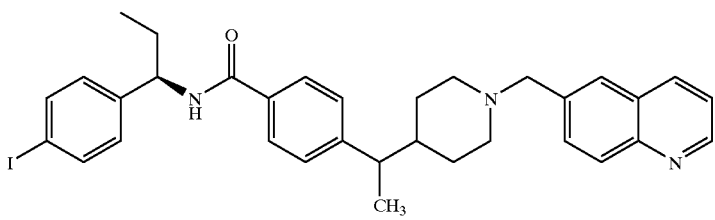

Step 1:

To a stirring solution of 11 (4 gm) in THF (20 ml) at −78° C. add CH₃MgBr (11 ml of a 3M solution in THF). After 30 min, warm to rt and then heat the reaction mixture at reflux temperature for 1 h and partition between saturated NH₄Cl and EtOAc. Wash the organic layers with 1N HCl and H₂O, dry over MgSO₄ and concentrate to dryness. Dissolve the residue (2.2 g) in CH₂Cl₂ (30 ml), add triethylsilane (15 ml) and TFA (15 ml). After stirring overnight, concentrate the reaction mixture under reduced vacuum (135° C. @ 2 mm Hg) to provide a yellow solid. Dissolve the solid (0.96 gm) in CH₂Cl₂ (30 ml), add (BOC)₂O (1.6 g) and 1 N NaOH (20 ml). After 2 h, separate the organic layer, wash with 1 N HCl, and dry over MgSO₄. Concentrate the mixture under reduced pressure (1 mm Hg, 100° C.) to provide compound 11A as light yellow oil (1.14 g).

Step 2:

To a solution of 11A (0.37 gm) in THF (10 ml) cooled to −78° C., add n-BuLi (0.6 ml of a 2.5 M solution in hexane) with stirring. After 30 min at −78° C., add a solution of 1-(4-iodophenyl)-propylisocyanate (prepare this from R-α-ethyl-4-iodobenzylamine from example 1, step 2, by reaction with triphosgene and proton sponge). After 15 min. add a solution of NH₄Cl and partition with CH₂Cl₂. The CH₂Cl₂ layers are separated and concentrated and the residue purified by prep TLC using 1:3 EtOAc:Hex to yield a colorless oil (0.91 g). Treat this oil with 10% TFA in CH₂Cl₂ (5 ml) for 2 h, then concentrate to dryness. Suspend a portion of this material (0.026 g) in CH₂Cl₂, add 6-quinolinecarboxaldehyde (0.016 g) and NaBH(OAc)₃ (0.014 g). Stir the reaction overnight, then purify by prep TLC using EtOAc to give the title compound as a yellow oil. LCMS Rt 5.26 min., observed mass 618.1 (M+H).

Using the same procedure as above but using piperonal in place of 6-quinolinecarboxaldehyde provides example 3a:

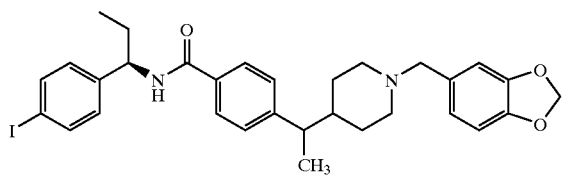

LCMS Rt 5.51 min., observed mass 611.1 (M + H)

EXAMPLE 4

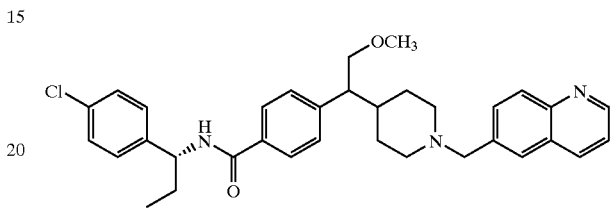

Step 1:

To CH₃Ph₃Br (13.58 g, 38 mmol, 2 eq) in THF (65 ml) at −78° C. was added n-BuLi (2.5 M in hexane, 15.2 ml, 2 eq) dropwise. The mixture was warmed to 0° C. and then cooled back to −78° C. before the ketone 11 (7 g, 1 eq)/30 ml THF) solution was transferred to the anion solution. 15 min later, the solution was warmed up to rt. After 1 h, the reaction was quenched by water. Extraction with ether and flash chromatography (EtOAc:Hexane, 1:6) gave the olefin 11f as clear oil (6.7 g, 97%).

¹HNMR (CDCl₃): δ 1.30 (m, 1H), 1.41 (s, 9H), 1.60 (m, 1H), 1.80 (m, 2H), 2.50 (m, 1H), 2.75 (m, 2H), 4.20 (, 2H), 5.01 (s, 1H), 5.20 (s, 1H), 7.20 (d, 2H, J=8.3 Hz), 7.41 (d, 2H, J=8.3 Hz).

Step 2:

Hydroboration of the 11f was done with 9-BBN and the alcohol was obtained in 97% yield. ¹HNMR (CDCl₃): δ 1.00 (m, 1H), 1.10–1.38 (m, 4H), 1.40 (s, 9H), 1.60–1.80 (m, 3H), 2.40–2.60 (m, 2H), 2.60–2.70 (m, 1H), 3.60 (m, 2H), 3.90–4.20 (m, 2H), 7.00 (d, 2H, J=8.1 Hz), 7.40 (d, 2H, J=8.1 Hz).

The alcohol (0.63 g, 1.64 mmol, 1 eq) was stirred with NaH (60%, 0.13 g, 2 eq), n-Bu₄NBr (0.2 g) in THF (5 ml) for 40 min before CH₃I (1 ml) was added. The mixture was stirred at 40° C. for 2 h. After extraction with EtOAc, flash chromatography (EtOAc:Hexane, 1:3) gave the methyl ether 11 g (0.45 g, 69%).

¹HNMR (CDCl₃): δ 0.99 (m, 1H), 1.10–1.38 (m, 4H), 1.40 (s, 9H), 1.60–1.80 (m, 3H), 2.40–2.60 (m, 2H), 2.60–2.70 (m, 1H), 3.20 (s, 3H), 3.60 (m, 2H), 3.90–4.20 (m, 2H), 7.00 (d, 2H, J=8.1 Hz), 7.40 (d, 2H, J=8.1 Hz).

Step 3:

11g (0.45 g, 1.13 mmol, 1 eq) was dissolved in THF (6 ml) and cooled to −78° C. under N₂. N-BuLi (2.5 M in hexane, 0.54 ml, 1.2 eq) was added dropwise and stirred for 5 min, then (R)-α-ethyl-4-chlorobenzylisocyanate (0.26 g, 1.2 eq) was added [Prepared from the amine (1 g, 5.90 mmol, 1 eq) by treatment with diphosgene (0.85 ml, 1.2 eq) and proton sponge (2.53 g, 2 eq) in 10 ml CH₂Cl₂). After 30 min, the crude was washed with 1 M HCl and 1 M NaOH. Flash chromatography (EtOAc:hexane, 1:5) provided 0.9 g of colorless liquid which was used immediately. ¹HNMR (CDCl₃): δ 1.00 (t, 3H, J=7.3 Hz), 1.80 (m, 2H), 4.5 (t, 1H, J=7.3 Hz), 7.20 (d, 2H, J=8.3 Hz), 7.30 (d, 2H, J=8.3 Hz)]. The crude was stirred for −78° C. for 1 h and warmed up to rt for another hour. After quenching with water and extraction, flash chromatography (EtOAc:hexane, 1:3) provided 11h (0.40 g, 69%).

¹HNMR (CDCl₃): δ 1.00 (t, 3H, J=7.0 Hz), 1.10–1.25 (m, 2H), 1.40 (s, 9H), 1.60–1.90 (m, 4H), 2.40–2.65 (m, 3H), 3.22 (s, 3H), 3.40 (m. 2H), 3.80–4.20 (m, 2H), 5.00 (q, 1H, J=7.2 Hz), 6.60 (d, 1H, J=7.7 Hz), 7.20 (d, 2H, J=7.1 Hz), 7.25 (s, 4H), 7.70 (d, 2H, J=7.0 Hz). ¹³CNMR (CDCl₃): δ 12.12, 29.64, 30.28, 31.34, 31.59, 39.53, 52.43, 55.91, 60.15, 75.11, 80.44, 128.01, 129.06, 129.62, 129.69, 133.66, 133.88, 141.90, 147.50, 155.63, 167.68. HRMS for C₂₉H₄₀ClN₂O₄ (M+1) calcd: 262.0093; found: 262.0092.

Step 4:

11h (87 mg, 0.169 mmol, 1 eq) was dissolved in CH₂Cl₂ (0.5 ml) and treated with 4 M HCl/dioxane (3 ml) for 24 h. The solvent was removed and the crude was basified with saturated NaHCO₃. Extraction with EtOAc provided 80 mg of the crude which was treated with 6-formylquinoline (80 mg, 3 eq) and NaBH(OAc)₃ (107 mg, 3 eq) in 5 ml CH₂Cl₂ for 24 h. The crude was washed with saturated Na₂CO₃ followed by extraction with CH₂Cl₂. Flash chromatography (CH₂Cl₂:CH₃OH:NH₄OH, 98:2:1) provided 60 mg of the desired product 11i.

¹HNMR (CDCl₃): δ 0.99 (t, 3H, J=7.3 Hz, 1.20 (m, 2H), 1.40 (m, 1H), 1.60 (m, 1H), 1.90 (m, 4H), 2.02 (m, 1H), 2.60 (m, 1H), 2.80 (d, 1H, J=12.1 Hz), 2.99 (d, 1H, J=11.7 Hz), 3.20 (s, 3H), 3.60 (m, 2H), 3.62 (s, 2H), 5.00 (q, 1H, J=7.5 Hz), 6.58 (d, 1H, J=7.9 Hz), 7.20 (d, 2H, J=8.3 Hz), 7.22 (m, 3H), 7.38 (m, 1H), 7.70 (m, 4H), 8.00 (d, 1H, J=8.0 Hz), 8.10 (d, 1H, J=8.3 Hz), 8.90 (d, 1H, J=4.0 Hz)

EXAMPLE 5

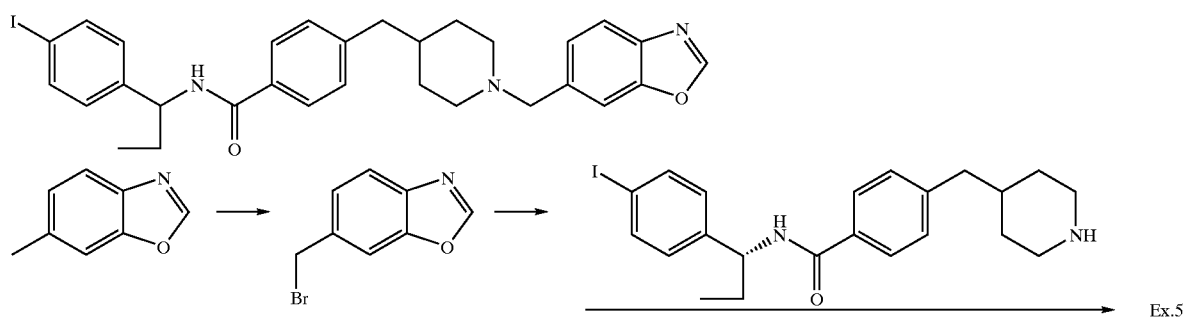

6-Methylbenzoxazole was reacted with NBS (1 eq) and catalytic amount of benzoyl peroxide in CCl₄ at 90° C. for 12 h to obtain 6-bromomethylbenzoxazole which was purified by flash chromatography (EtOAc:Hexane=1:5).

¹HNMR (CDCl₃): δ 4.60 (s, 2H), 7.42 (d, 1H, J=8.2 Hz), 7.64 (s, 1H), 7.76 (d, 1H, J=8.2 Hz), 8.12 (s, 1H). The product (42 mg, 1.5 eq) was immediately reacted with the piperidine derivative (62 mg, 1 eq) with K₂CO₃ in CH₃CN (3 ml) at 80° C. under N₂ overnight. Direct chromatography (CH₂Cl₂:CH₃OH:NH₄OH, 98:2:1) gave the desired product (8.4 mg).

¹HNMR (CDCl₃): δ 1.00 (t, 3H, J=7.3 Hz), 1.20–1.40 (m, 2H), 1.50–1.70 (m, 3H), 1.80–2.00 (m, 4H), 2.60 (d, 2H, J=6.6 Hz), 2.90 (d, 2H, J=10.5 Hz), 3.60 (s, 2H), 5.00 (q, 1H, J=7.6 Hz), 6.38 (d, 1H, J=7.9 Hz), 7.05 (d, 2H, J=8.2 Hz), 7.19 (d, 2H, J=8.1 Hz), 7.30 (d, 1H, J=8.1 Hz), 7.60 (s, 1H), 7.62–7.70 (dm, 5H). HRMS for C₃₀H₃₃IN₃O₂ (M+1) calcd: 594.1618; found: 594.1612.

EXAMPLE 6

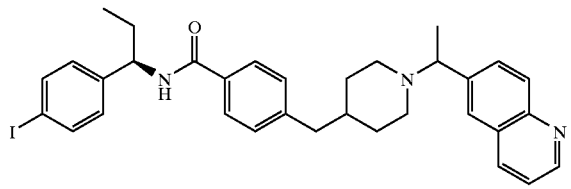

Compound 14 (150 mg, 0.325 mmol) is dissolved in dry CH₂Cl₂ under N₂, Ti(Oi—Pr)₄ (0.144 ml, 0.487 mmol) and quinoline-6-carboxaldehyde (77 mg, 0.487 mmol) are added and stirred overnight. The reaction is cooled to 0° C. under N₂, CH₃MgBr (0.325 ml of 3M solution, 0.975 mmol) is added dropwise, THF (1 ml) is added, and the reaction is stirred for 4 h. The reaction is quenched with water, and EtOAc and 1N NaOH are added. The mixture is filtered through celite, the organic layer is separated and washed with sat. NaCl, dried over Na₂SO₄, and purified by flash chromatography with CH₂Cl₂/2N NH₃ in CH₃OH (97/3) to obtain the title compound. LCMS Rt 7.06 min., observed mass 618.1 (M+H).

Using the same procedure, but with piperonal in place of quinoline-6-carboxaldehyde, gives Example 6a:

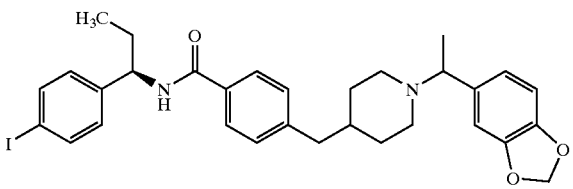

LCMS Rt 5.01 min., 611.1 obs. mass (M + H)

EXAMPLE 7

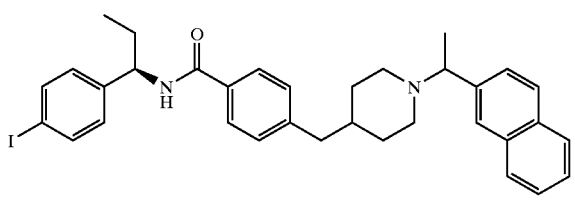

14 (100 mg, 0.22 mmol) and 1-(2-napthyl)-chloroethane (63 mg, 0.33 mmol) are suspended in 4-methyl-2-pentanone (3 ml). $Na_2CO_3$ (466 mg, 4.4 mmol) and KI (4.0 mg, 0.022 mmol) are added into the above mixture, and the sealed tube is heated at 80° C. overnight. The reaction mixture is cooled to rt, filtered and washed with $CH_2Cl_2$, the $CH_2Cl_2$ solution is concentrated and purified by flash chromatography with $CH_2Cl_2$/2N $NH_3$ in $CH_3OH$ (97:3) to yield the title compound. LCMS Rt 5.51 min., observed mass 617.1 (M+H).

Use the same procedure, but with 6-(1-[methylsulfonyloxy]propyl)-quinoline (prepared from the corresponding alcohol by reaction with $CH_3SO_2Cl$ and DIPEA in ether) in place of 1-(2-napthyl)-chloroethane to obtain Example 7a:

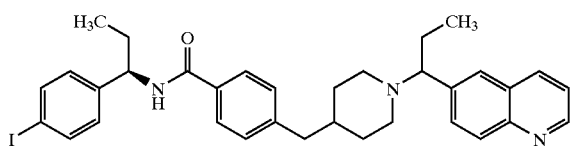

LCMS Rt 5.16 min. 632.1 obs. mass (M + H)

Use the same procedure but with 1-(4-bromophenyl)-chloroethane in place of 1-(2-napthyl)-chloroethane to obtain Example 7b:

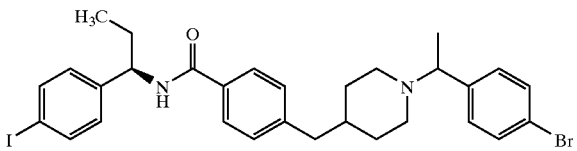

LCMS Rt 5.23 min. obs. mass 647.2 (M + H)

EXAMPLE 8

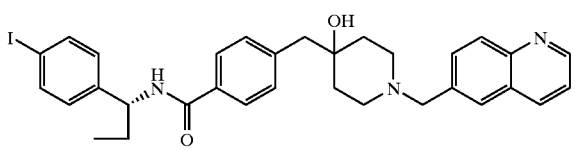

Step 1:

To 15 (10.1 g, 20.14 mmol, 1 eq)/90 ml anhydrous THF was added KHMDS (0.5 M, 44 ml, 1.1 eq) at rt under $N_2$. After stirring for 1 h, the ketone (see Scheme 5) (4.8 g, 1.2 eq) was added and the mixture was heated to 90° C. for 24 h. The reaction was quenched by water and extracted with EtOAc. The organic layer was dried with $MgSO_4$ and flash chromatography (EtOAc:hexane, 1:10) afforded 15a as white solid (4.15 g, 62% yield).

$^1$HNMR (CDCl$_3$): δ 1.40 (s, 9H), 2.38 (m, 2H), 2.42 (m, 2H), 3.40 (m, 2H), 3.70 (m, 2H), 3.90 (s, 3H), 6.40 (s, 1H), 7.20 (d, 2H, J=8.3 Hz), 8.00 (d, 2H, J=8.3 Hz).

Step 2:

Intermediate 15a (0.9 g, 2.72 mmol, 1 eq) was dissolved in $CH_2Cl_2$ (10 ml) at rt and MCPBA (1.87 g, 50%, 2 eq) for 24 h. 10% $Na_2SO_3$ (10 ml) was added and the organic layer was further washed with $NaHCO_3$. After drying with $MgSO_4$, the solvent was removed and the residue redissolved in $CH_3OH$. Pd/C (0.1 g) was added the reaction was conducted under $H_2$ balloon at rt for 3 h. After filtration through celite, flash chromatography (EtOAc:hexane, 1:1) provided 15b as white solid (0.59 g, 56% yield).

$^1$HNMR (CDCl$_3$): δ 1.30–1.60 (m, 4H), 1.40 (s, 9H), 2.78 (s, 2H), 3.00–3.16 (m. 2H), 3.70–3.90 (m, 2H), 3.88 (s, 3H), 7.20 (d, 2H, J=8.2 Hz), 7.90 (d, 2H, J=8.2 Hz). $^{13}$CNMR (CDCl$_3$): δ 29.64, 29.69, 30.28, 37.84, 50.49, 53.23, 70.70, 80.57, 129.52, 130.43, 131.55, 142.83, 155.69, 167.88. HRMS for $C_{19}H_{28}NO_5$ (M+1) calcd: 350.1967; found: 350.1968.

Step 3:

15b (0.56 g, 0.968 mmol, 1 eq) was stirred with LiOH.H$_2$O (40 mg) in THF (2 ml), $CH_3OH$ (2 ml) and H$_2$O (2 ml ) at 40° C. for 20 h. The solvent was removed and the solution was treated with concentrated HCl to pH 1. Extraction with $CH_2Cl_2$ afforded 0.45 g acid in 84% yield.

$^1$HNMR (CDCl$_3$): δ 1.40–1.65 (m, 4H), 1.42 (s, 9H), 2.80 (s, 2H), 3.00–3.20 (m. 2H), 3.80–3.95 (m, 2H), 3.88 (s, 3H), 7.30 (d, 2H, J=8.2 Hz), 8.00 (d, 2H, J=8.2 Hz).

The acid (215 mg, 0.371 mmol, 1 eq) was mixed with R-α-ethyl-4-iodobenzylamine (97 mg, 1 eq), HATU (142 mg, 1 eq), Hunig's base (0.14 ml, 2 eq) in 1 ml of DMF and stirred for 1.5 h. The crude was extracted with EtOAc and dried over $MgSO_4$. After removal of the solvent, the crude was treated with 4M HCl/dioxane (2 ml) for 5 h. The solvent was removed and basified with saturated $Na_2CO_3$. Extraction with $CH_2Cl_2$ several times and then removal of the solvent provided the desired product. It was then immediately treated with 6-formylquinoline (65 mg, 1.1 eq) and NaBH(OAc)$_3$ (89 mg, 1.1 eq) in $CH_2Cl_2$ (5 ml) for 39 h. The crude was washed with saturated $Na_2CO_3$ followed by extraction with $CH_2Cl_2$. Flash chromatography ($CH_2Cl_2$: $CH_3OH$:NH$_4$OH, 98:2:1) provided 39 mg of the title compound in 23% yield.

$^1$HNMR (CDCl$_3$): δ 0.98 (t, 3H, J=7.4 Hz), 1.30 (br s, 1H), 1.50 (d, 2H, J=13.2 Hz), 1.70–1.80 (m, 2H), 1.80–2.00 (m, 2H), 2.35 (t, 2H, J=10.9 Hz), 2.62 (d, 2H, J=11.2 Hz), 2.80 (s, 2H), 3.62 (s, 2H), 5.00 (q, 1H, J=7.5 Hz), 6.30 (d, 1H, J=7.6 Hz), 7.05 (d, 2H, J=8.2 Hz), 7.24 (d, 2H, J=7.6 Hz), 7.40 (dd, 1H, J=4.2, 8.2 Hz), 7.60–7.77 (m, 6H), 8.02 (d, 1H, J=9.1 Hz), 8.10 (d, 1H, J=8.8 Hz), 8.90 (d, 1H, J=4.1 Hz). HRMS for $C_{32}H_{35}IN_3O_2$ (M+1) calcd: 620.1774; found: 620.1769.

Using the procedure in step 3 with 15a as starting material, Example 8A was obtained:

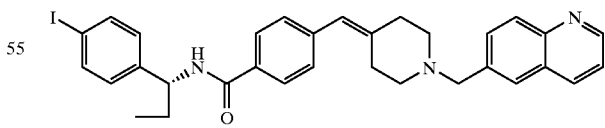

$^1$HNMR (CDCl$_3$): δ 0.99 (t, 3H, J=7.2 Hz), 1.80–1.90 (m, 2H), 2.40–2.70 (m, 8H), 3.73 (s, 2H), 5.00 (q, 1H, J=7.2 Hz), 6.29 (s, 1H), 6.32 (d, 1H, J=8.0 Hz), 7.09 (d, 2H, J=8.0 Hz), 7.20 (d, 2H, J=8.2 Hz), 7.40 (dd, 1H, J=4.4, 8.3 Hz), 7.65 (d, 2H, J=8.3 Hz), 7.69 (d, 2H, J=8.0 Hz), 7.76 (d, 1H, J=7.2 Hz), 8.07 (d, 1H, J=8.8 Hz), 8.13 (d, 1H, J=8.0 Hz), 8.88 (d, 1H, J=4.0 Hz). HRMS for $C_{32}H_{33}IN_3O$ (M+1): calcd: 602.1668; found: 602.1657.

45

The compound of Example 8B

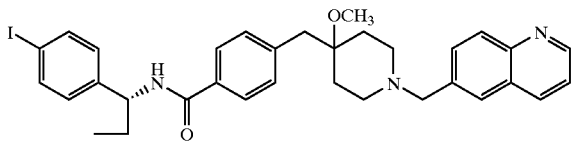

was prepared from the tertiary alcohol 15b (0.19 g, 0.54 mmol, 1 eq) by dissolving in anhydrous THF (5 ml) and treating with NaH (60%, 0.2 g, 10 eq) and CH$_3$I (1 ml). The mixture was stirred at rt overnight. After quenching the reaction with CH$_3$OH, the solvent was removed and extraction with CH$_2$Cl$_2$ followed by flash chromatography (EtOAc:Hexane, 1:3) provided the desired methyl ether (46 mg, 23%).
$^1$HNMR (CDCl$_3$): δ 1.42 (s, 9H), 1.35–1.50 (m, 2H), 1.60–1.70 (m, 2H), 2.80 (s, 2H), 2.90–3.10 (m, 2H), 3.38 (s, 3H), 3.70–3.85 (m, 2H), 3.90 (s, 3H), 7.20 (d, 2H, J=8.1 Hz), 7.99 (d, 2H, J=8.1 Hz).
The methyl ether was treated with LiOH.H$_2$O (58 mg) in 1 ml water/0.5 ml THF/0.5 ml CH$_3$OH at 40° C. for 60 h. The solvent was removed and the pH was adjusted to 1. Extraction with EtOAc and drying over MgSO$_4$ gave the corresponding acid (45 mg).
$^1$HNMR (CDCl$_3$): δ 1.42 (s, 9H), 1.40–1.50 (m, 2H), 1.60–1.70 (m, 2H), 2.80 (s, 2H), 2.90–3.10 (m, 2H), 3.40 (s, 3H), 3.70–3.85 (m, 2H), 7.20 (d, 2H, J=8.1 Hz), 8.02 (d, 2H, J=8.1 Hz).
The acid (45 mg) was treated with R-α-ethyl-4-iodobenzylamine (37 mg, 1.1 eq), HATU (49 mg, 1 eq) and 2 eq of Hunig's base in 0.5 ml DMF for 24 h. After workup, 74 mg of the crude was obtained. The material was dissolved in 4 M HCl/dioxane (2 ml) and stirred overnight. After removal of the solvent, the crude was basified to pH 10 and extracted with EtOAc. About one half of the obtained product (30 mg, 0.061 mmol) was treated with 6-formylquinoline (76 mg, 8 eq) and NaBH(OAc)$_3$ (103 mg, 8 eq) in 4 ml CH$_2$Cl$_2$ for 22 h. The crude was washed with saturated Na$_2$CO$_3$ followed by extraction with CH$_2$Cl$_2$. Flash chromatography (CH$_2$Cl$_2$:CH$_3$OH:NH$_4$OH, 98:2:1) provided 32 mg of the title compound.
$^1$HNMR (CDCl$_3$): δ 0.98 (t, 3H, J=7.3 Hz), 1.50–1.70 (m, 4H), 1.80–1.90 (m, 2H), 2.2–2.00–2.40 (m, 2H), 2.55–2.70 (m, 2H), 2.78 (s, 2H), 3.30 (s, 3H), 3.70 (s, 2H), 4.90 (s, 1H), 5.00 (q, 1H, J=7.3 Hz), 6.40 (d, 1H, J=8.0 Hz), 7.05 (d, 2H, J=8.1 Hz), 7.18 (d, 2H, J=8.0 Hz), 7.40 (m, 1H), 7.60–7.80 (m, 5H), 8.02 (m, 1H), 8.10 (d, 1H, J=8.0 Hz), 8.95 (m, 1H).

EXAMPLE 9

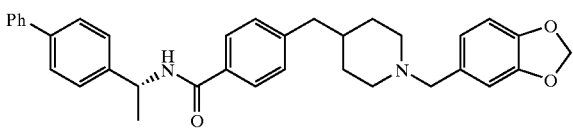

The iodide analog on the Argopore-MB-CHO resin (prepared as described in the general synthesis procedures, 100 mg, 0.7 mmol/g, 0.07 mmol) was mixed with phenylboronic acid (42 mg), Pd(PPh$_3$)$_4$ (8 mg), K$_2$CO$_3$ (100 mg) in 0.5 ml DMF. The mixture was stirred under Ar at 40° C. for 12 h. The crude was washed with 5% KCN/DMF, water, CH$_3$OH, CH$_2$Cl$_2$, and the final product was cleaved with 10% TFA/CH$_2$Cl$_2$ and dried as TFA salt. LC-MS Rt 4.83 min., observed mass 533 (M+H).

Using this procedure and the appropriate aromatic halides the examples in Table 3 of the formula

46

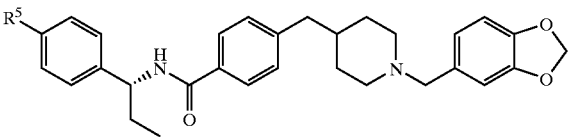

wherein R$^5$ is defined in the table, were prepared.

| Ex. | R$^5$ | Rt(min) | Obs. Mass (m + H) |
|---|---|---|---|
| 9-1 | 3-acetylphenyl | 4.36 | 589 |
| 9-2 | phenyl | 4.61 | 547 |
| 9-3 | 3-nitrophenyl | 4.56 | 592 |
| 9-4 | 2,4-dichlorophenyl | 5.26 | 615 |
| 9-5 | 1-naphthyl | 5.06 | 597 |
| 9-6 | 3-methylphenyl | 4.86 | 561 |
| 9-7 | 3-chloro-4-fluorophenyl | 4.96 | 599 |
| 9-8 | 3,5-dichlorophenyl | 5.46 | 615 |

-continued
| Ex. | R⁵ | Rt(min) | Obs. Mass (m + H) |
|---|---|---|---|
| 9-9 | 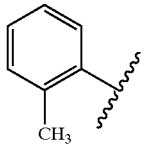 | 4.86 | 561 |
| 9-10 | 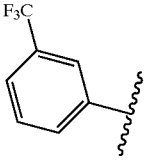 | 5.01 | 615 |
| 9-11 | 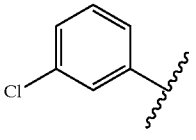 | 4.96 | 581 |
| 9-12 | 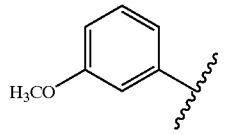 | 4.61 | 577 |
| 9-13 | 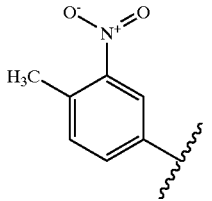 | 4.76 | 606 |
| 9-14 | 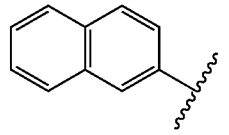 | 5.16 | 597 |
| 9-15 | 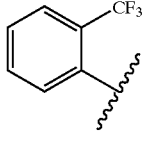 | 4.86 | 615 |
| 9-16 | 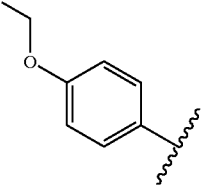 | 4.86 | 591 |
-continued
| Ex. | R⁵ | Rt(min) | Obs. Mass (m + H) |
|---|---|---|---|
| 9-17 | 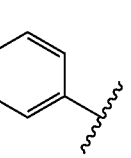 | 5.16 | 575 |
| 9-18 | 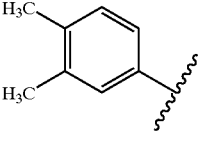 | 5.16 | 575 |
| 9-19 | 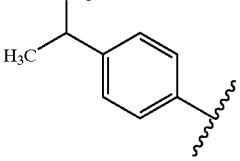 | 5.46 | 589 |
| 9-20 | 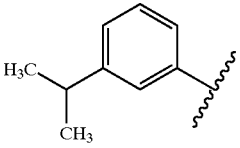 | 5.36 | 589 |
| 9-21 | 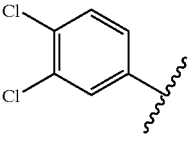 | 5.31 | 615 |
| 9-22 | 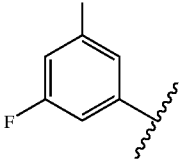 | 4.81 | 583 |
| 9-23 | 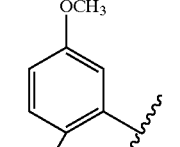 | 4.56 | 607 |
| 9-24 | 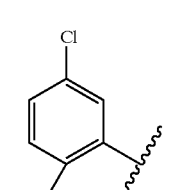 | 4.96 | 611 |

-continued

| Ex. | R⁵ | Rt(min) | Obs. Mass (m + H) |
|---|---|---|---|
| 9-25 | 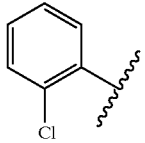 | 4.86 | 581 |
| 9-26 | 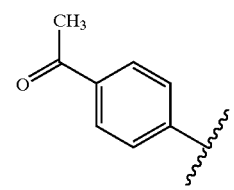 | 4.36 | 589 |
| 9-27 | 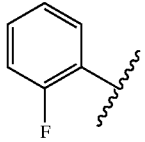 | 4.71 | 565 |
| 9-28 | 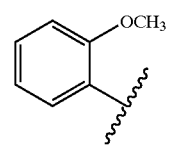 | 4.71 | 577 |

-continued

| Ex. | R⁵ | Rt(min) | Obs. Mass (m + H) |
|---|---|---|---|
| 9-29 | 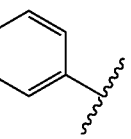 | 4.96 | 561 |
| 9-30 | 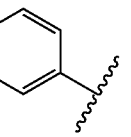 | 5.06 | 581 |
| 9-31 | 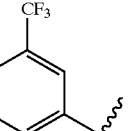 | 5.36 | 683 |
| 9-32 | 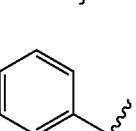 | 4.66 | 577 |

EXAMPLE 10

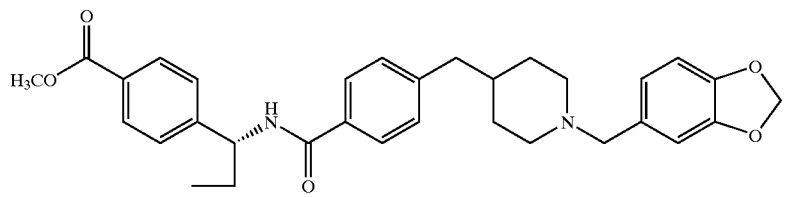

The iodide analog on the Argopore-MB-CHO resin (100 mg, 0.7 mmol/g, 0.07 mmol) was mixed with Pd(OAc)$_2$ (50 mg), Et$_3$N (0.2 ml) and Ph$_3$P (0.1 g) in CH$_3$OH (10 ml). The mixture was stirred under CO atmosphere at 50° C. for 12 h. The crude was washed with water, CH$_3$OH, CH$_2$Cl$_2$ and the final product was cleaved with 10% TFA/CH$_2$Cl$_2$ and dried as TFA salt. Flash chromatography (CH$_2$Cl$_2$:CH$_3$OH:NH$_4$OH, 98:2:1) gave the desired product (19 mg).

$^1$HNMR (CDCl$_3$): δ 1.00 (t, 3H, J=7.4 Hz), 1.30 (m, 2H), 1.50 (m, 3H), 1.70–2.00 (m, 4H), 2.58 (d, 2H, J=6.8 Hz), 2.90 (d, 2H, J=11.5 Hz), 3.40 (s, 2H), 3.90 (s, 3H), 5.10 (q, 1H, J=7.6 Hz), 5.99 (s, 2H), 6.40 (d, 1H, J=7.8 Hz), 6.70 (s, 2H), 6.80 (s, 1H), 7.20 (d, 2H, J=8.2 Hz), 7.40 (d, 2H, J=8.3 Hz), 7.66 (d, 2H, J=8.3 Hz), 8.00 (d, 2H, J=8.3 Hz). LC-MS Rt 4.36 min., observed mass 528 (M+H).

What is claimed:
1. A compound represented by the structural formula

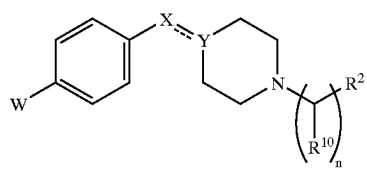

I or a pharmaceutically acceptable salt, ester or solvate thereof, wherein

W is $R^1$—$CR^3R^{12}NR^4C(O)$—;
the dotted line is an optional double bond;
X is —$CHR^8$—, —$C(O)$—, —$C(=NOR^9)$—, or, when the double bond is present, —$CR^8$=;
Y is

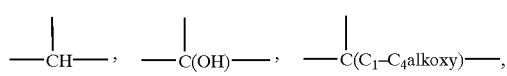

or, when the double bond is present,

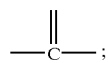

$R^1$ is $R^5$—$(C_3-C_8)$cycloalkyl, $R^5$—$(C_3-C_8)$cycloalkyl $(C_1-C_8)$alkyl, $R^5$-aryl, $R^5$-aryl-$(C_1-C_6)$alkyl, $R^5$-heteroaryl, $R^5$-heteroaryl$(C_1-C_6)$alkyl, $R^5$-heterocycloalkyl or $R^5$-heterocycloalkyl$(C_1-C_6)$alkyl;
$R^2$ is $R^6$-aryl or $R^6$-heteroaryl;
n is 1, 2 or 3;
$R^3$ is $C_1-C_6$ alkyl, aryl or heteroaryl;
$R^4$ is H or $C_1-C_6$ alkyl;
$R^5$ is 1–4 substituents independently selected from the group consisting of H, $C_1-C_6$ alkyl, halogen, —OH, $C_1-C_6$ alkoxy, —$CF_3$, $(C_1-C_6)$-alkoxycarbonyl, —$SO_2NHR^4$, —$C(O)NHR^4$, —$NR^4C(O)NHR^4$, —$NR^4C(O)R^4$, —$NR^4SO_2R^4$, $R^{13}$-phenyl and naphthyl;
$R^6$ is 1–4 substituents independently selected from the group consisting of H, $C_1-C_6$ alkyl, halogen, —OH, —SH, —$S(C_1-C_6$ alkyl), —CN, $C_1-C_6$ alkoxy, $C_1-C_6$ alkylcarboxy, $CF_3$, —$NO_2$, —$NH_2$, $(C_1-C_6)$ alkylamino, phenyl, $(C_1-C_6)$-alkoxycarbonyl and $R^7$-phenoxy, or adjacent ring carbon atoms form a ring with the group —$O(CH_2)_{1-2}O$—, —O $(CH_2)_{2-3}$— or —$O(CF_2)O$—;
$R^7$ is 1–3 substituents independently selected from the group consisting of H, $C_1-C_6$ alkyl, halogen, —OH, $C_1-C_6$ alkoxy and $CF_3$;
$R^8$ is H, $C_1-C_6$ alkyl or $(C_1-C_4)$alkoxy-$(C_1-C_4)$alkyl;
$R^9$ is H, $C_1-C_6$ alkyl or aryl-$(C_1-C_4)$alkyl;
$R^{10}$ is independently selected from the group consisting of H, $C_1-C_6$ alkyl and aryl;
$R^{12}$ is H or $C_1-C_6$ alkyl; and
$R^{13}$ is 1 to 3 substituents independently selected from the group consisting of H, $C_1-C_6$ alkyl, halogen, —OH, $C_1-C_6$ alkoxy, —$CF_3$, —$OCF_3$, —$NO_2$ and —$C(O)CH_3$.

2. A compound of claim 1 wherein $R^1$ is $R^5$-phenyl.
3. A compound of claim 2 wherein $R^5$ is H, halogen, $C_1-C_6$ alkyl or phenyl.
4. A compound of claim 1 wherein $R^2$ is $R^6$-aryl.
5. A compound of claim 4 wherein $R^{10}$ is H or $C_1-C_6$ alkyl and n is 1.
6. A compound of claim 5 wherein $R^2$ is phenyl.
7. A compound of claim 1 wherein $R^3$ is ethyl or methyl, $R^4$ is H and $R^{12}$ is H.
8. A compound of claim 1 wherein X is —$CHR^8$ and Y is CH.
9. A compound of claim 1 wherein X and Y form a double bond.
10. A compound of claim 1 selected from the group consisting of compounds of the formula

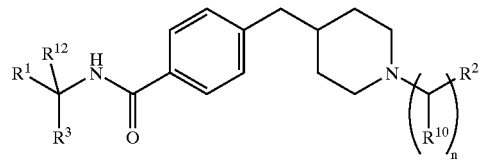

wherein

   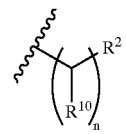

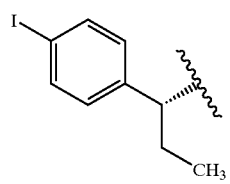   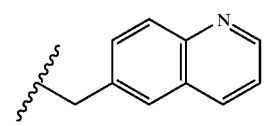

-continued
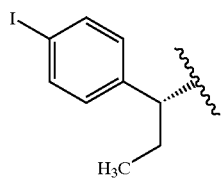 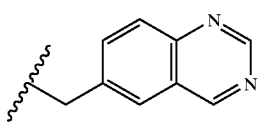
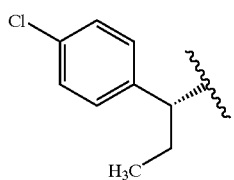 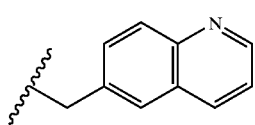
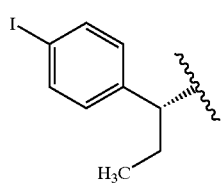 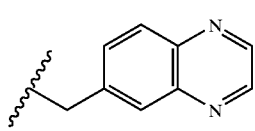
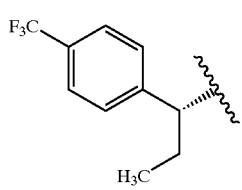 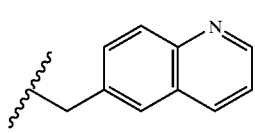
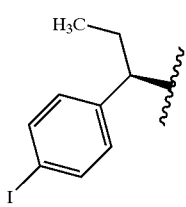 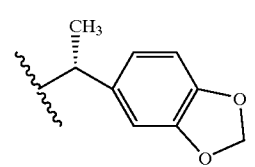
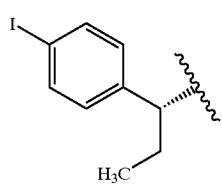 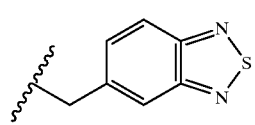
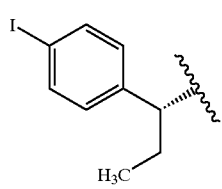 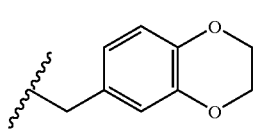
and compounds of the formula
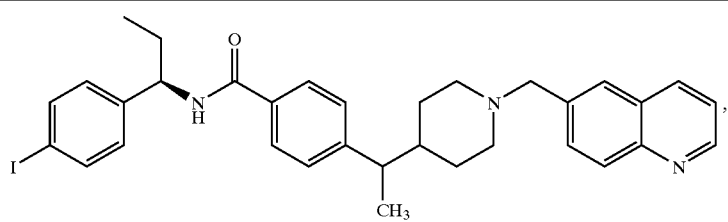

-continued
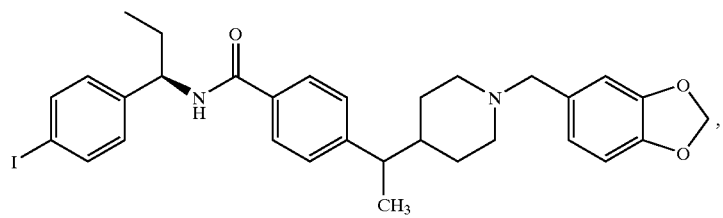
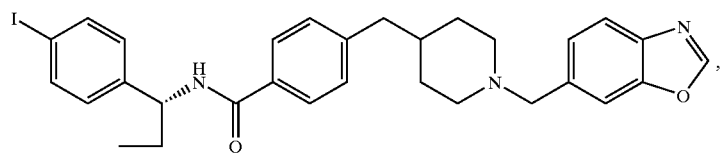
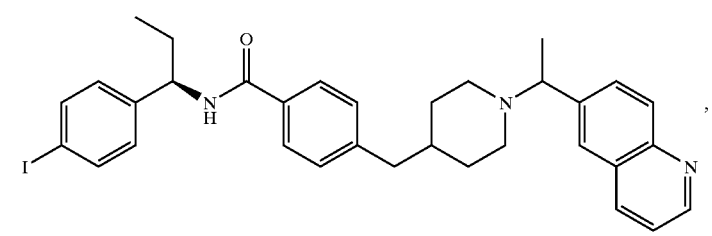
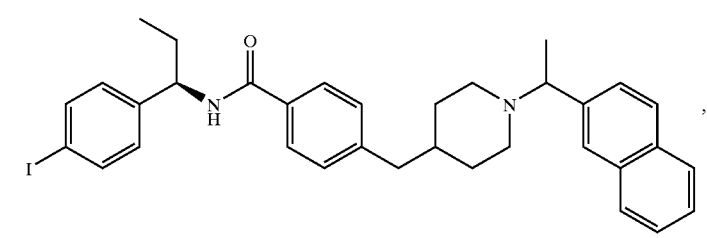
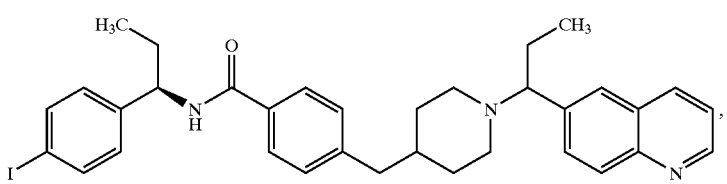
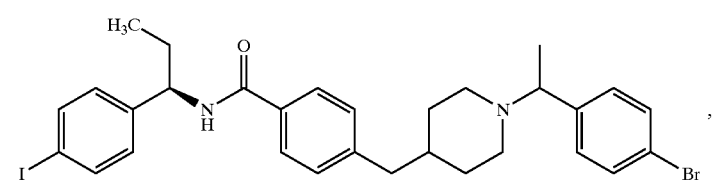
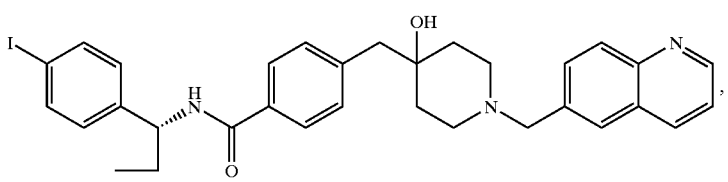
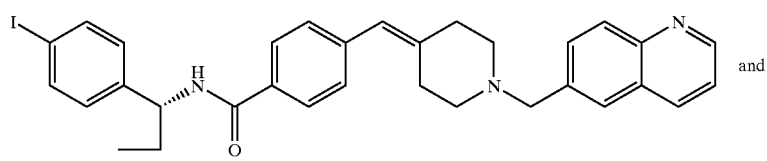
and -continued
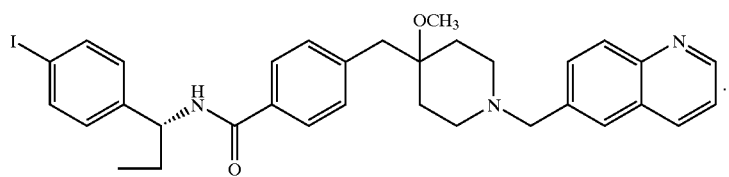
11. A pharmaceutical composition comprising a therapeutically effective amount of a compound of claim 1 in combination with a pharmaceutically acceptable carrier.
12. A method of treating an eating disorder or diabetes comprising administering an effective amount of a compound of claim 1 to a mammal in need of such treatment.
* * * * *